United States Patent
Vera et al.

(10) Patent No.: US 10,568,763 B2
(45) Date of Patent: Feb. 25, 2020

(54) SYSTEMS AND METHODS TO DELIVER PHOTODISRUPTIVE LASER PULSES INTO TISSUE LAYERS OF THE ANTERIOR ANGLE OF THE EYE

(71) Applicants: Vanessa I Vera, Mission Viejo, CA (US); Christopher Horvath, Mission Viejo, CA (US)

(72) Inventors: Vanessa I Vera, Mission Viejo, CA (US); Christopher Horvath, Mission Viejo, CA (US)

(73) Assignee: FSEYE, LLC, San Juan Capistrano, CA (US)

( * ) Notice: Subject to any disclaimer, the term of this patent is extended or adjusted under 35 U.S.C. 154(b) by 601 days.

(21) Appl. No.: 14/685,955

(22) Filed: Apr. 14, 2015

(65) Prior Publication Data
US 2015/0305939 A1 Oct. 29, 2015

Related U.S. Application Data

(62) Division of application No. 13/442,854, filed on Apr. 10, 2012, now Pat. No. 9,033,963.

(51) Int. Cl.
*A61B 5/06* (2006.01)
*A61F 9/008* (2006.01)
*A61F 9/007* (2006.01)
*A61F 9/009* (2006.01)

(52) U.S. Cl.
CPC .......... *A61F 9/00821* (2013.01); *A61F 9/009* (2013.01); *A61F 9/00781* (2013.01); *A61F 9/00825* (2013.01); *A61F 2009/00868* (2013.01); *A61F 2009/00891* (2013.01)

(58) Field of Classification Search
CPC .............. A61F 9/00821; A61F 9/00781; A61F 9/00825; A61F 2009/00868; A61F 2009/00891
USPC ....................................................... 606/4, 6
See application file for complete search history.

(56) References Cited

U.S. PATENT DOCUMENTS

| | | | |
|---|---|---|---|
| 6,450,984 B1 * | 9/2002 | Lynch | A61F 9/00781 604/284 |
| 2008/0181362 A1 * | 7/2008 | Gertner | A61N 5/1017 378/65 |
| 2009/0157062 A1 * | 6/2009 | Hauger | A61B 3/102 606/5 |

* cited by examiner

*Primary Examiner* — Aaron F Roane

(57) ABSTRACT

The invention relates to systems and methods for accessing tissue layers of the anterior chamber angle of an eye, targeting one or multiple treatment zones within the anterior angle area of the eye and delivering focused photodisruptive laser pulses with pulse durations <50 picoseconds creating channels into various anatomical structures within the anterior angle of the eye.

6 Claims, 25 Drawing Sheets

SYSTEMS AND METHODS TO DELIVER PHOTODISRUPTIVE LASER PULSES INTO TISSUE LAYERS OF THE ANTERIOR ANGLE OF THE EYE

CROSS-REFERENCE TO RELATED APPLICATIONS

This is a division of application Ser. No. 13/442,854 filed on Apr. 10, 2012. This application further claims the benefit of the U.S. provisional application No. 61/473,806, filed Apr. 10, 2011, the content of which is considered incorporated by reference herein in its entirety. To the extent the following description is inconsistent with the disclosure of the provisional application, the following description controls.

BACKGROUND OF THE INVENTION

Lasers have been used for several decades in the treatment of glaucoma. The 2 most common laser treatments for primary open angle glaucoma (POAG) are ALT (Argon Laser Trabeculoplasty) and SLT (Selective Laser Trabeculoplasty). See for example U.S. Pat. Nos. 3,884,236; 8,066,696; 5,549,596; 6,319,274. They work by applying laser pulses into the Trabecular Meshwork (in the anterior angle of the eye). These laser pulses are focused to around 50 micrometer diameter for ALT and around 400 micrometer for SLT. Those laser spots are targeted to lay over Schlemm's canal and cause an increased outflow through the treated Trabecular meshwork area. In both procedures at least 180 degrees of the eye angle is treated with typically 50 to 100 laser pulses (each pulse is applied to a new target zone-treatment area). The working mechanism for ALT is blanching of the Trabecular meshwork that increases the outflow by stretching the Trabecular Meshwork between the blanched (laser treated areas). The ALT laser with a typical setting of 600 mW and 0.1 s pulse duration (at 514 nm or 532 nm) causes a thermal tissue interaction. In SLT treatment the laser causes cavitation bubbles in the target tissue due to its shorter pulse duration of about 3 nanoseconds and higher peak power (created by pulse energies of around 0.3 mJ to 1.6 mJ).

Both procedures have a good success rate by increasing aqueous humor outflow that creates a substantial drop in intraocular pressure of around 20%. Both procedures can be performed in minutes with a simple slit lamp procedure in the office (no OR visit required). In both procedures, the eye does not need to be opened (non-invasive procedure), therefore the treatment risks and complication rates are minimal. The problem of these procedures as published in many studies is that it does not work effectively in all patients and in the successful cases the effect wears off over the course of a few (1-3 years) and the IOP rises back to its baseline level. The procedure can be repeated once with ALT and 2-3 times with SLT, but after those repeats the tissue damage in the Trabecular meshwork that is created through those multiple procedures ultimately prevents any further IOP lowering effect.

A less frequently used laser procedure called ELT (Excimer Laser Trabeculostomy) uses an Excimer laser pulse (wavelength in the UV range) to actually drill holes into the Trabecular Meshwork. See for example U.S. patent applications: 20080082078; 20040082939. Because complete openings are created to Schlemm's canal (unlike ALT and SLT), the IOP lowering effect is similar or better than ALT/SLT and in the same time only a few open holes need to be drilled with ELT versus 50-100 treatment zones in a typical ALT/SLT procedure. Some studies further suggest that the ELT effect is longer lasting then ALT/SLT due to some observed long term patency of those holes. Furthermore ELT might be repeated more often since a smaller area of the Trabecular Meshwork is treated each time. The downside of ELT is the fact that UV wavelength light does not penetrate the cornea and aqueous humor, therefore the laser can only be applied to the Trabecular Meshwork in an operating room procedure, where the eye is opened and a fiber probe is inserted into the anterior chamber all the way up to the Trabecular Meshwork.

In recent years the effectiveness of having one or multiple holes in the Trabecular Meshwork (connecting to Schlemm's canal) has also been demonstrated with several implants, placed through the Trabecular Meshwork that create an opening into Schlemm's canal. See for example U.S. patent applications: 20120071809, 20070276316. Those are however also invasive (full operating room) procedures using an implant.

Another approach to drain aqueous humor out of the anterior chamber has been successfully demonstrated by implanting a drainage tube through the scleral spur region and into the suprachoroidal space. See for example U.S. patent application: 20110098629. This is however also an invasive (full operating room) procedures using an implant.

Most recently, there have been animal tissue studies applying ultrashort photodisruptive laser pulses to the trabecular meshwork with limited success. Hiroshi Nakamura et. al. Investigative Ophthalmology & Visual Science, March 2009, Vol. 50, No. 3. Performed an ex vivo study on primates delivering photodisruptive laser pulses into the anterior angle of the eye. He presents several limitations and challenges in the paper concerning the goal of creating a hole through the Trabecular Meshwork. These limitations and challenges have so far prevented a successful use of such a non-invasive laser procedure in the angle of the eye.

The inventions described herein relate to a new devices and methods to overcome those limitations and challenges and therefore allow the creation of holes and channels in the Trabecular Meshwork and other places in the angle of the eye in a non-invasive procedure that can be repeated as many times as necessary.

Other examples of related prior art are U.S. Pat. Nos. 8,056,564; 4,391,275; 5,288,288; 7,912,100

BRIEF SUMMARY OF THE INVENTION

Photodisruptive laser pulses in the range of <1000 femtoseconds have been successfully applied to make incisions into various tissues of the eye. The main focus to date has been using a femto second laser for various cornea incisions such as LASIK flaps, intrastromal incisions, Limbal Relaxing Incisions, Keratoplasties and cornea entry incisions. In more recent years femtosecond lasers have also been successfully applied to the capsule and the lens of the human eye in femtosecond laser assisted cataract procedures.

The main benefit of these photodisruptive laser pulses lays in the fact that the eye tissues, that are treated transmit the wavelengths of the typically chosen lasers, usually in the near infrared or visible range and therefore allow the laser to be focused through the cornea, aqueous humor, lens capsule and lens without much scattering or absorption. The laser pulses are always focused to a very small spot size in the range of a few micrometers, where a laser induced optical breakdown is achieved in any tissue or liquid (e.g. aqueous humor) that falls within the spot size location.

This optical breakdown (photodisruptive breakdown) creates a micro plasma followed by a small cavitation bubble, which can be used to cut and dissect tissue areas of any size and shapes by scanning a sequence of many such laser pulses over a desired volume in the eye.

Since the tissue layers in the laser path above and below the focus point are below the optical breakdown threshold and since they mostly the laser wavelength, they remain unaffected by the laser beam. This principle allows non-invasive photo disruptive eye surgery since no incision from the outside needs to be made.

There is a threshold of a minimum laser fluence (laser peak power divided by focus area) required to achieve the optical breakdown. The laser peak power goes up no with higher pulse energy (typically in the μJ range) and shorter pulse duration (typically <600 fs). The laser fluence for any given peak power goes up as the focus area goes down. Achieving a small spot size is therefore critical in achieving a high fluence that exceeds the optical breakdown threshold.

The way of achieving a high enough fluence for breakdown by increasing the us laser pulse energy is less desirable since a higher pulse energy comes with a larger cavitation bubble and associated shock wave. The larger the cavitation bubble the less precision is achieved in cutting any features with a sequence of pulses. Furthermore a large shock wave is considered a undesired side effect since it has the potential to damage surrounding tissues.

Priority is therefore given to minimizing the spot size to achieve an above threshold laser fluence while using laser pulses within a low pulse energy range of <50 μJ per laser pulse.

These principles have been successfully implemented in femto second eye laser systems treating the cornea or capsule/lens of an eye. The laser delivery systems can 125 achieve good focusing access to the cornea and lens through large focusing lens assemblies positioned within a few cm above the eye. Typical laser beam focusing convergence angles achieved are numerical apertures of NA>0.15 (full angle Θ>15 deg) and in some optimized cases NA>0.3.

According to:

$$\Theta = M^2 \frac{360 \lambda}{\pi^2 \omega_0}$$ Formula 1

Θ = full focusing convergence angle in degrees

λ = laser wavelength $\omega_0$ = laser beam focus radius defined by $1/e^2$ cut off $M^2$ = beam quality factor determined by the total aberrations If beam aberrations can be kept to a minimum e.g. $M^2$<1.3 ($M^2$=1 is the theoretical minimum with no aberration at all) then the above focusing angles of NA>0.15 (Θ>15 deg) and NA>0.30 (Θ>30 deg) the resulting spot size diameters ($2\omega_0$) will be <8 μm and <4 μm respectively (for a laser wavelength λ=1 μm).

The minimization of aberrations is critical in achieving such small spot sizes.

The tissue layers in the cornea and lens/capsule are relatively easy accessible for any laser beam from the outside.

Due to the fact that the existing systems focused laser beams enter the eye in a 145 straight vertical line that is perpendicular to the central area of the cornea (and top surface of any used patient interface) the aberrations can be kept small enough to allow small spot sizes. Such femtosecond cornea and lens/capsule systems typically reach beam quality factors of $M^2$<2.

The same easy access is not available for reaching the anterior camber angle tissue layers of the eye with a highly focused laser beam.

Furthermore the tissue layers in the anterior angle of the eye contain blood vessels that will start bleeding when hit or cut by photo disruptive laser pulses.

Therefore, there are several limitations and considerations that need to be overcome in order to deliver photo disruptive laser pulses to the anterior angle of the eye. Very limited success has been demonstrated so far in reaching these tissue layers (e.g. Trabecular Meshwork or scleral spur) with the goal of applying a laser pulse sequence that can create a drainage channel (hole) into and through those tissue layers.

Accessibility consideration factors for a highly convergent focused laser beam targeting the tissue layers of the anterior chamber angle:

Eye Anatomy:

The eye anatomy see FIG. 9 restricts the angular accessibility of the anterior angle (e.g. Trabecular Meshwork 3104) particularly in the vertical plane (defined here as a plane that includes the z-axis going centrally).

FIG. 3 shows a histology picture of the anterior angle in such a vertical cut. This eye shows a rather narrow angle of only 20 degrees. Typical angles in human eyes (including Primary Open Angle Glaucoma—POAG) are between 30 and 50 Degrees.

This vertical plane (vertical angle axis) represents the most restricted axis in terms of angular accessibility since the tangential access plane (the plane that includes the rim of the Trabecular Meshwork—perpendicular to the vertical plane) has a somewhat larger accessibility angle.

There are further factors limiting angular access to the eye (particular the already critical vertical plane).

Eye Geometry Variations:

The anterior angle accessibility varies widely from eye to eye. For example in highly myopic eyes the angle can be larger than 45 Degrees, while it becomes more narrow in Hyperopic eyes. FIG. 4 shows a more average 40 degree angle opening 3015.

Other Factors and Limitations of Anterior Angle Angular Access:

Total Internal Reflection, Gonioscopy Lens Requirement:

Due to the geometry of the cornea and anterior angle the light rays out of the anterior angle cannot exit the cornea due to total internal reflection. An optical interface with a similar index of refraction is therefore required on top of the cornea. This is called a gonioscopy lens (from here on referred to as a gonio lens). This invention includes several new gonio lens variations and designs that address and solve besides other features the wide angle laser delivery issues and limitations. FIG. 5 and FIG. 6 illustrate these principals.

Beam Aberrations:

The focusing laser beam has to go through several interfaces such as gonio lens, goniogel, cornea and aqueous humor. There are numerous cases of beam aberrations limiting the focusing power due to:

The wavefront of the beam hits many of those interfaces at high angles which is prone to cause astigmatism and higher order aberrations.

The interfaces curvatures such as the cornea vary from eye to eye and are not aberration free, especially at shallow incidence angles. The most upper vertical beam limit line runs at some point almost parallel to the cornea and endothelial cell layer. This causes significant aberrations in that part of the focusing laser beam. See for example FIG. 10.

The sagittal and tangential (vertical and horizontal) planes are exposed to significant different aberrations due to different interface curvatures in their respective planes.

The sagittal and tangential planes have different focusing requirements as discussed above (see FIG. 7) and therefore also experience different levels of aberrations.

All these factors need to be considered in the design and the methods of a delivery system, that can meet the small focusing requirements at the anterior angle. This invention addresses those limitations.

The limitations that need to be addressed and overcome can be summarized into the following categories:

The anatomical limitations of the human eye, in particular the relatively narrow access angle to the Trabecular Meshwork between the iris and the cornea are limiting the maximal possible focusing angle in that dimension. Furthermore human eyes show a great range of variability in this anatomical angle. In particular the last 1-2 mm before the actual chamber angle has great access variability between 0 deg (in case of a closed angle) to 50 deg opening based on the exact iris position.

Often the last 1 mm distance approaching the anterior angle from the center of the anterior chamber is hard to visualize even with a gonio lens a and can close off very rapidly due to iris synechia and iris bulging.

The laser beam cannot enter the eye perpendicular, but rather enters the cornea under a shallow and at some outer beam limits at an almost parallel angle. This dramatically increases the amount of aberrations that the laser beam wave front experiences during the beam propagation into the eye. Furthermore any contact interface and gonio lens that applies pressure to the cornea will induced aberrations such as cornea wrinkles that need to be overcome and/or compensated for.

The target region contains tissues of varying absorption and optical breakdown threshold characteristics since there is a great patient variability in pigmentation and presence of blood vessels or blood itself. These variations create large variability in the photo disruptive breakdown threshold fluency of the laser-tissue interactions and need to be considered and compensated for.

Due to total internal reflection, the angle is not directly accessible without the use of a gonio lens. A specific gonio lens design is required to minimize aberrations, allow for sufficient eye fixation and most importantly to allow transmission of a highly convergent laser beam as described above.

To allow integration of a gonio lens into a laser delivery system a patient interface with specific features is required.

The present inventions provides a method for overcoming the limitations described above. In particular the invention provides the following method:

A second method (as named in the parent application) to measure and maximize the vertical angular laser beam access and therefore achieving minimal spot size at the anterior angle tissue layers of an eye. The horizontal convergence angle of the treatment laser beam is fixed to preferably 60 deg (+/−20 deg) to create a small spot size 250 in the horizontal axis in the range of <10 μm diameter depending on the overall aberrations.

DETAILED DESCRIPTION OF THE INVENTION

Figure 9:
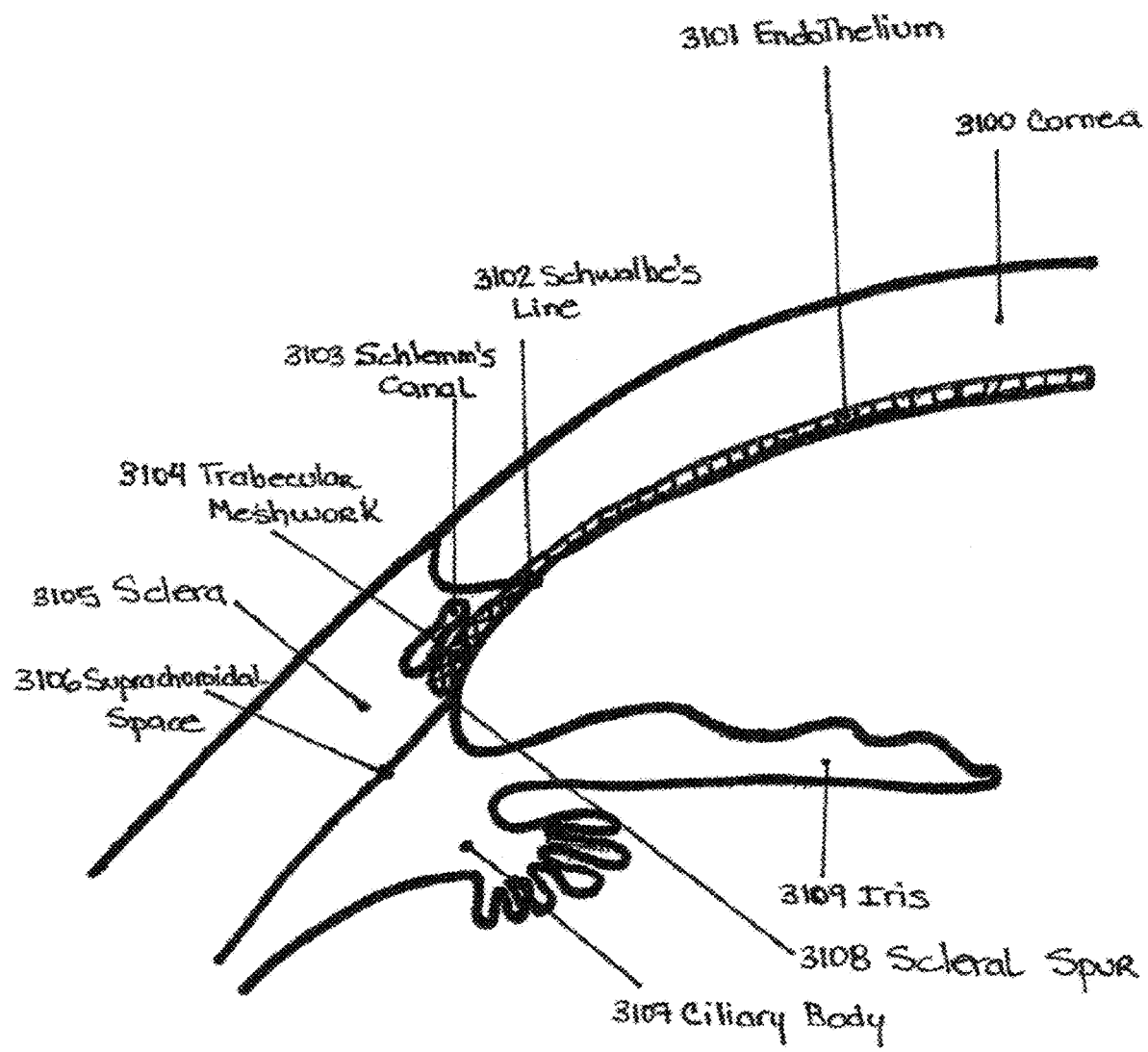
FIG. 9 shows the anatomical features of the anterior angle of an eye

The word "fs-laser" throughout this disclosure stands for femtosecond laser and is meant to cover any laser source, that can provide pulse durations smaller than <50000 femtoseconds (50 pico seconds) with a preferable range of 10 fs to 500 fs. The word femtosecond can also be interchanged with the word photodisruptive throughout the entire disclosure. This ultra-short pulse requirement together with a small spot size area (preferably <20 μm for circular focus and preferably <400 μm$^2$ for elliptical focus) allows the use of very small pulse energies in the range of <200 micro Joules (preferable range <50 micro joules) while still achieving a photodisruptive (plasma induced optical breakdown) tissue reaction that allows for the creation of a hole (tunnel) in tissue layers in the anterior angle of the eye (e.g the Trabecular Meshwork). FIG. 9 shows the anatomical features of the anterior angle area of the eye. It is critical to keep the pulse energies small since the undesired side effects such as shockwaves and large cavitation bubbles scale with the pulse energy, reduce precision and cause increasing collateral tissue damage around the desired target zone.

Figure 1:
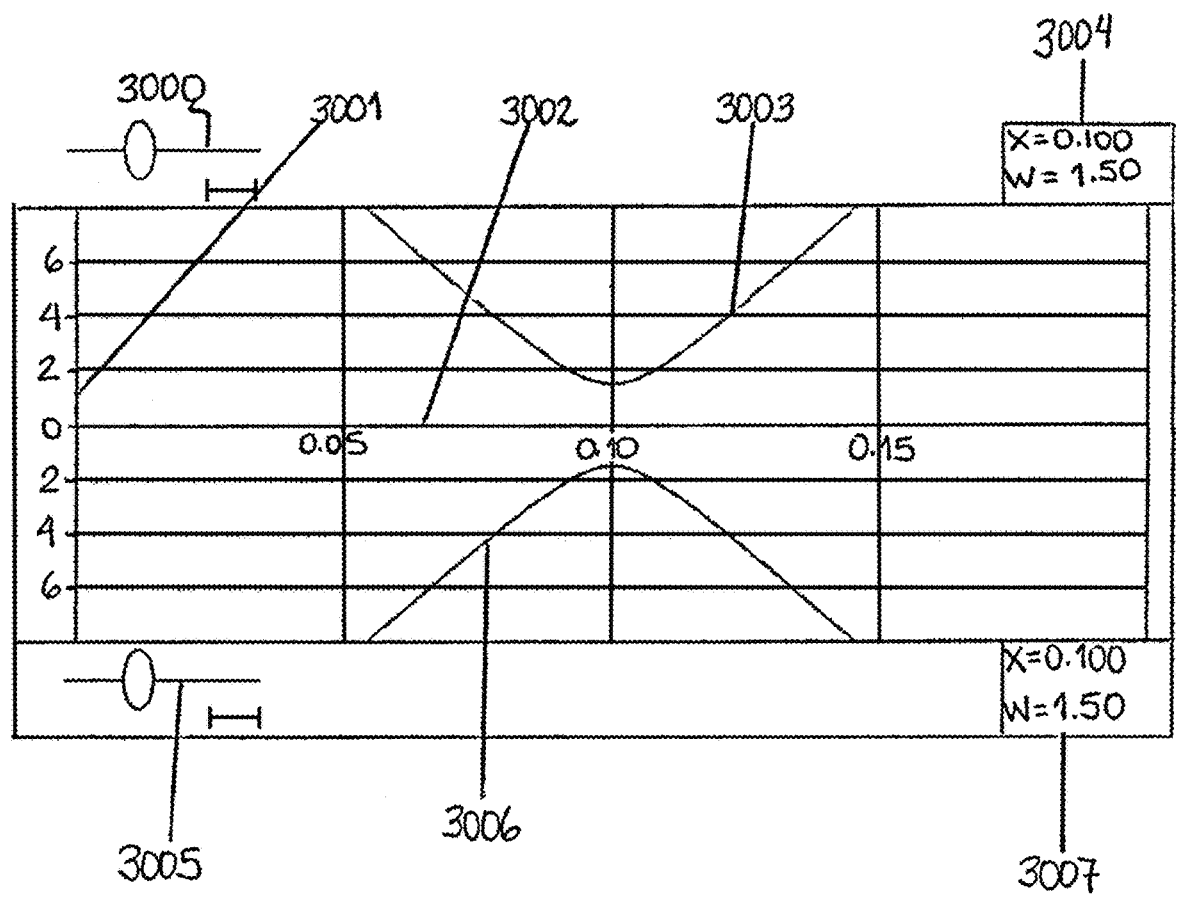
FIG. 1 illustrates a laser focus with a 3 μm diameter and a 20 deg convergence angle

FIG. 1. The small focus requirement leads to a large focusing beam convergence angle (high numerical aperture NA) in the range of 10-90 degrees. A 3 μm spot size diameter of a λ=1060 nm fs-laser beam with an aberration free beam quality factor of $M^2=1$ requires about 20 degrees ($1/e^2$) of full convergence (often referred to as beam divergence) angle as can be seen in the simulated coherent laser beam 3003 horizontal and 3006 vertical propagation calculation of FIG. 1.

Figure 2:
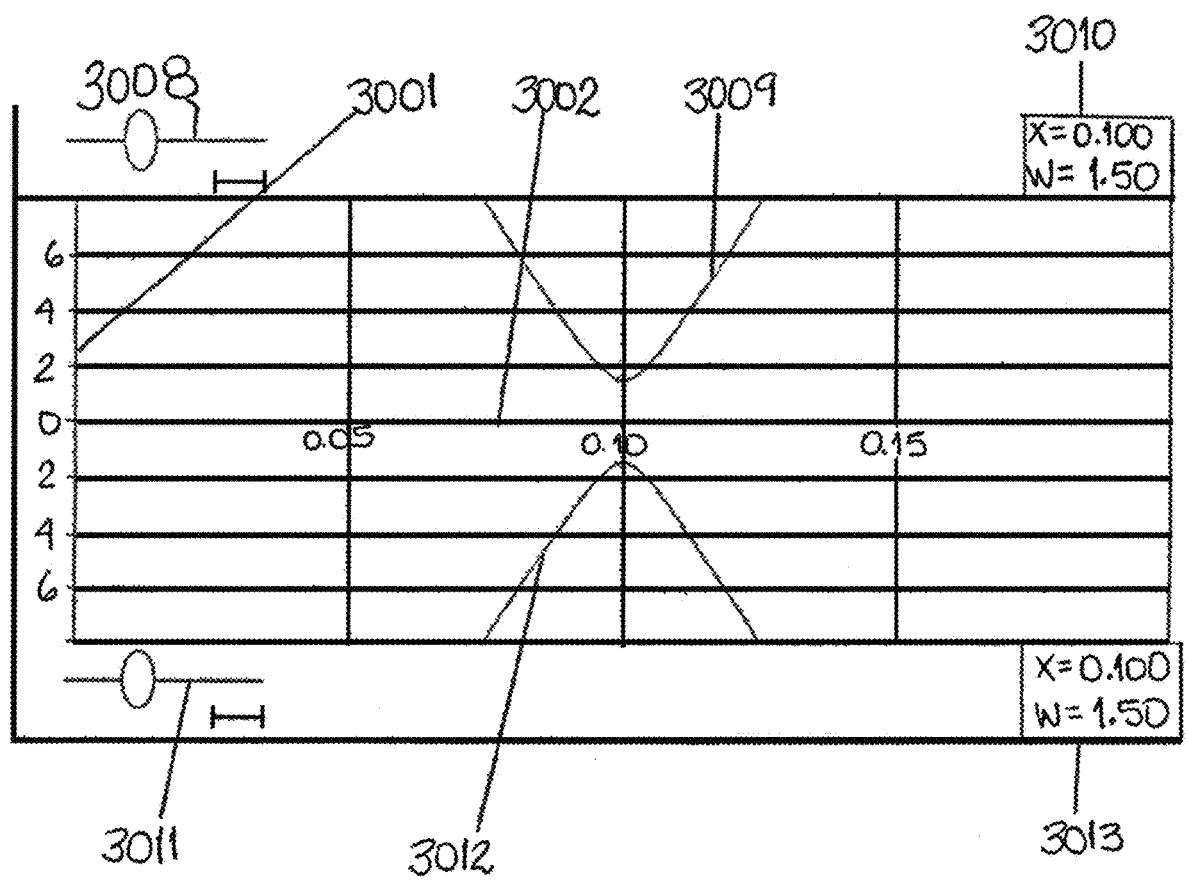
FIG. 2 illustrates a laser focus with a 3 μm diameter and a 40 deg convergence angle
Figure 3:
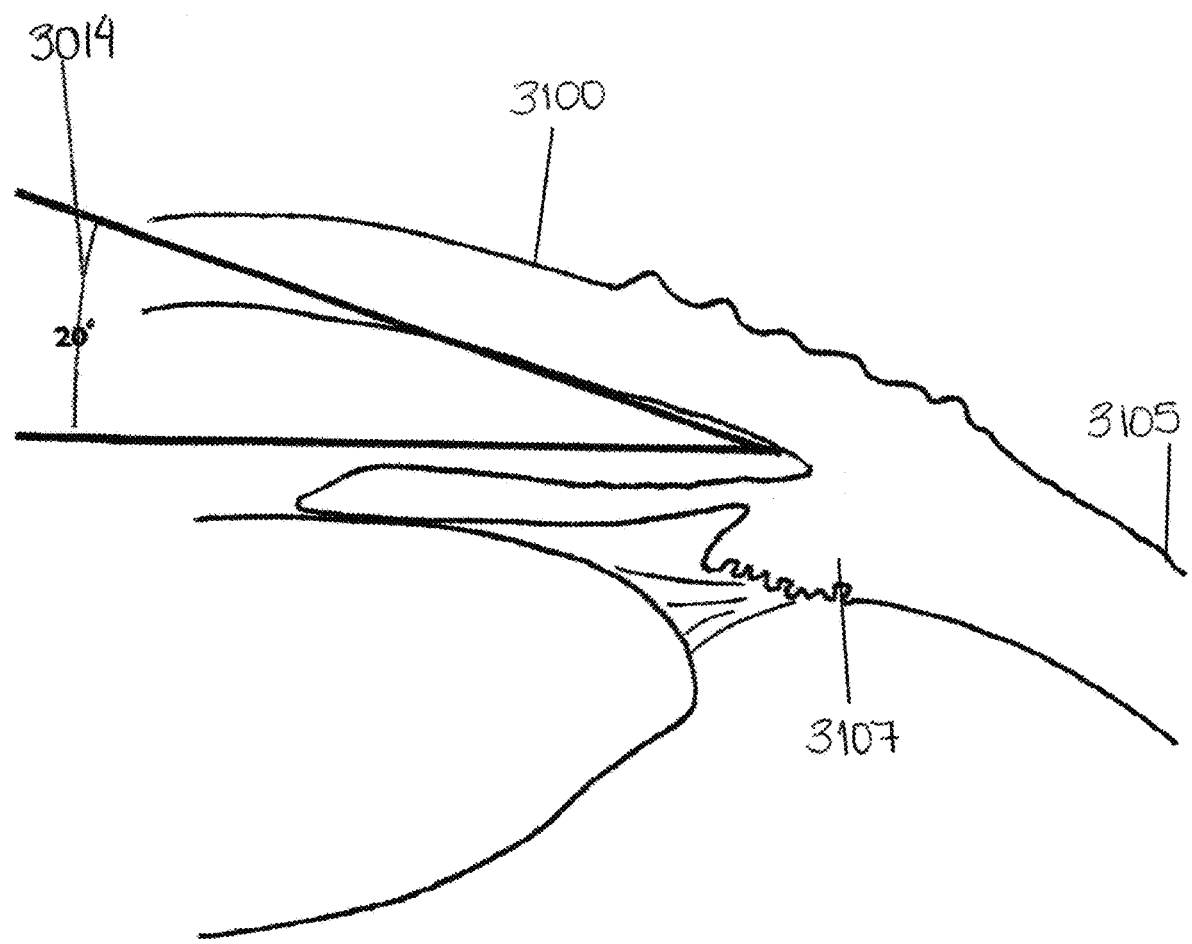
FIG. 3 illustrates a 20 deg laser focus into the anterior angle region of an eye
Figure 4:
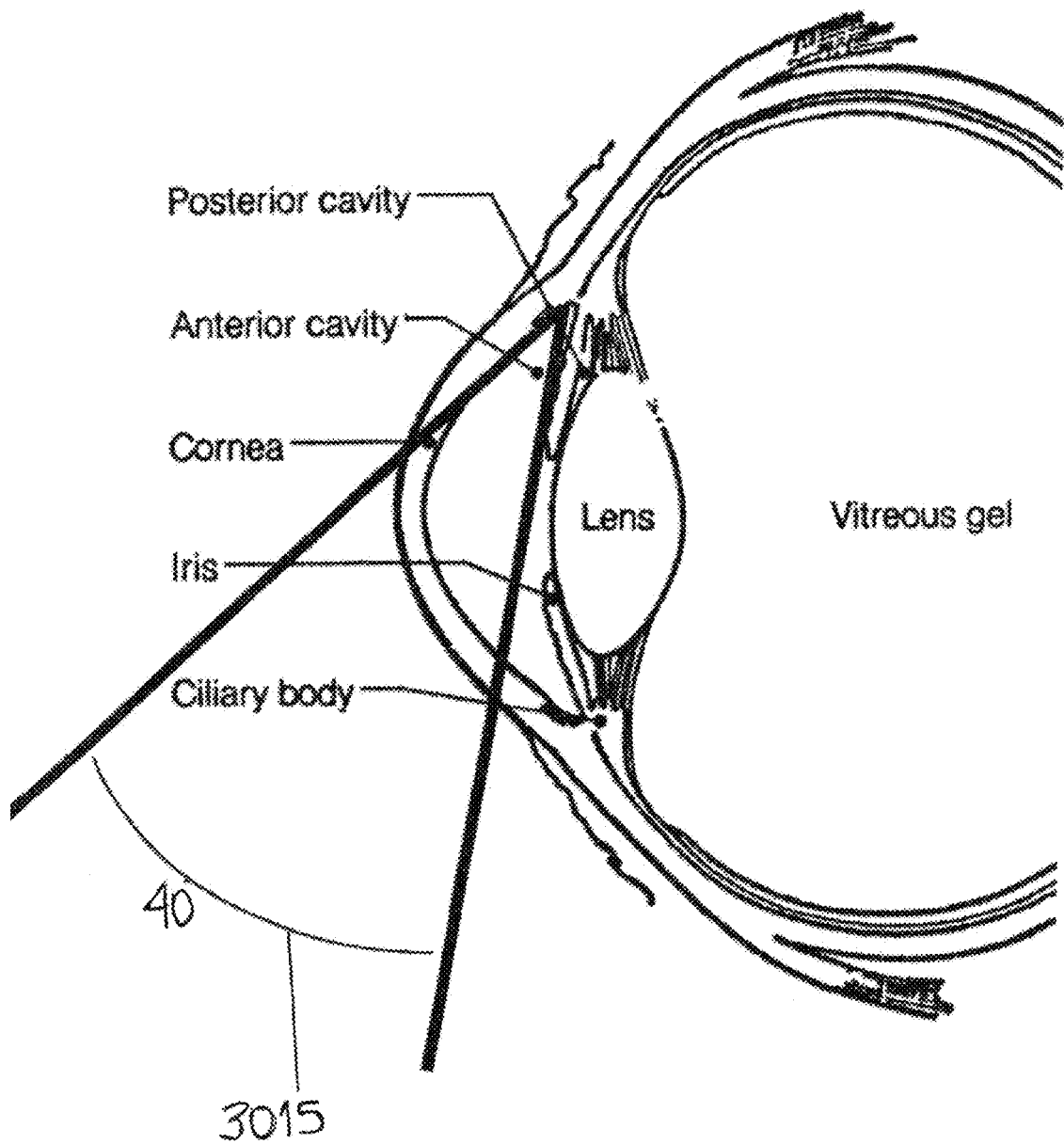
FIG. 4 illustrates a 40 deg laser focus into the anterior angle region of an eye
Figure 5:
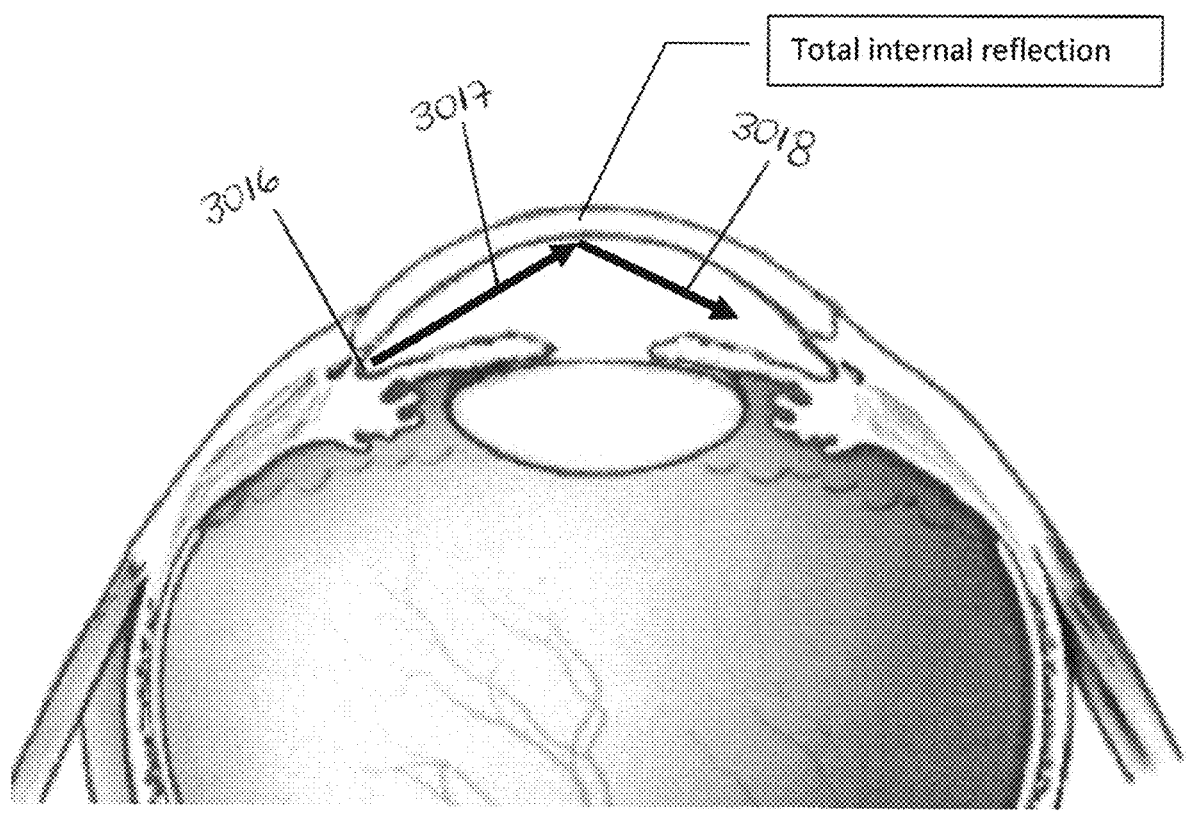
FIG. 5 shows the concept of total internal reflection
Figure 6:
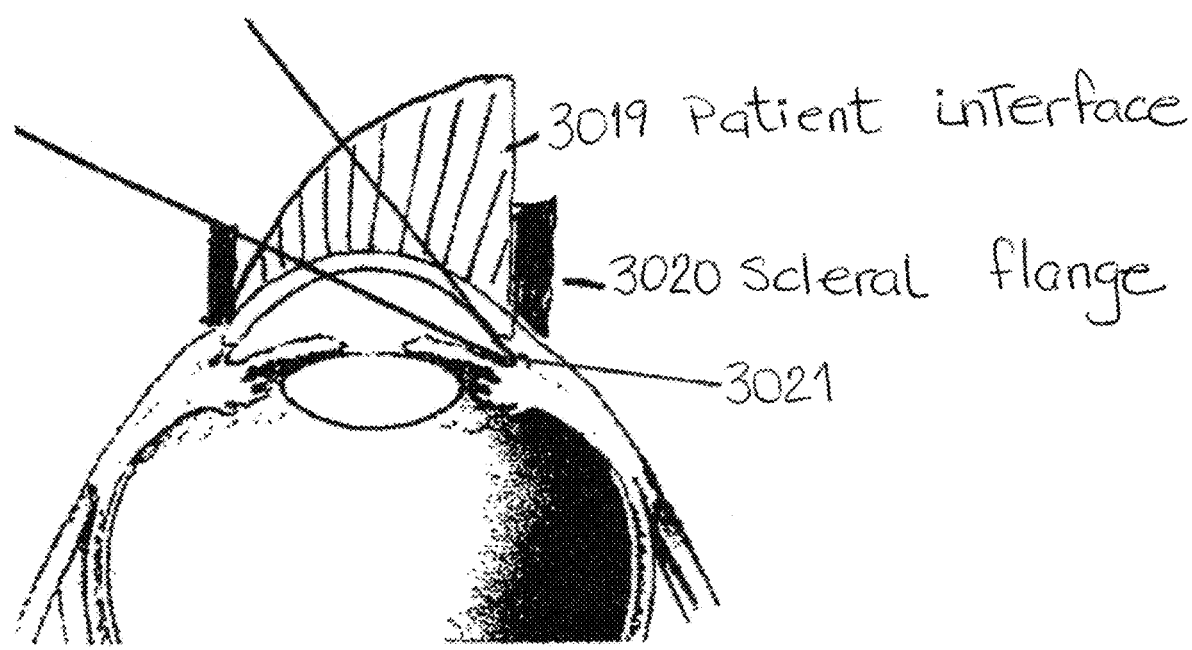
FIG. 6 illustrates a laser beam path using a direct gonio lens
Figure 7:
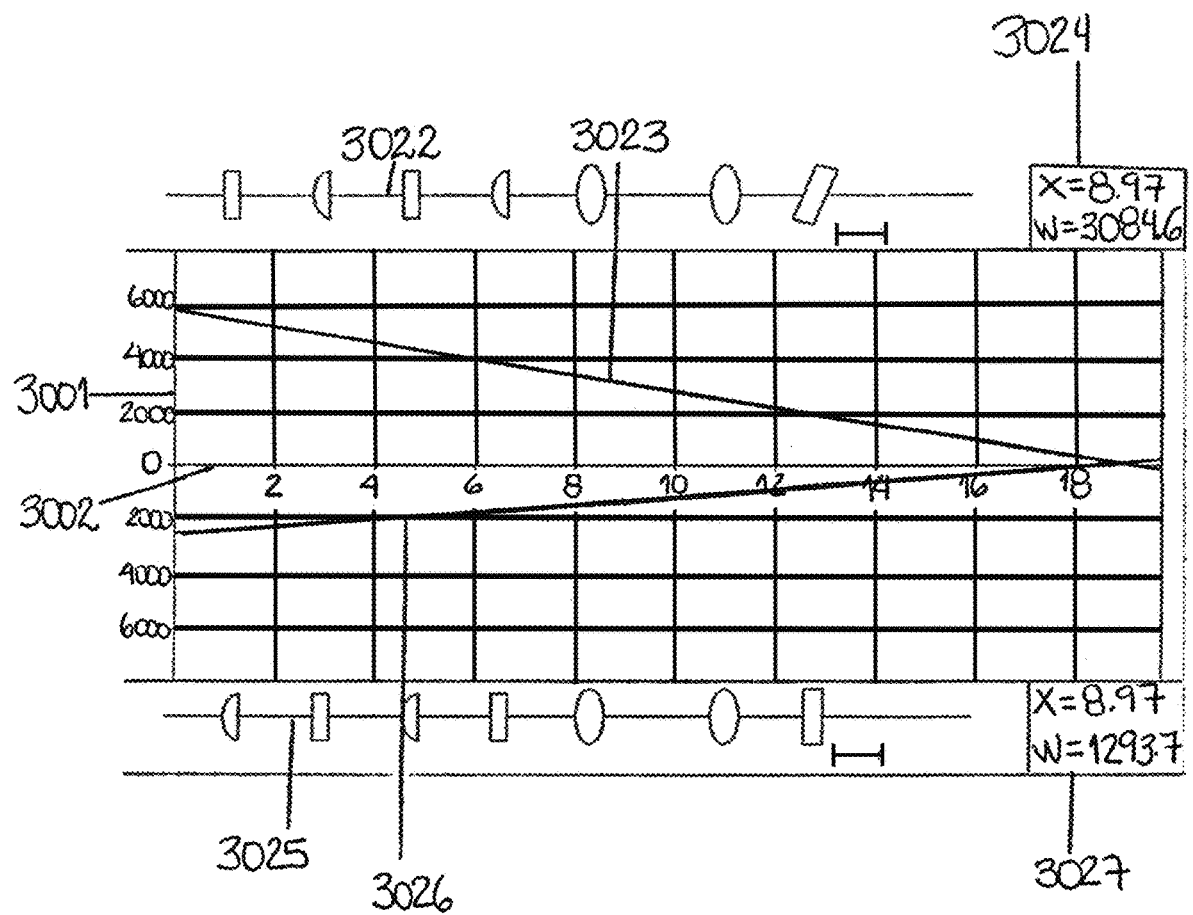
FIG. 7 shows a simulated laser beam with different focusing characteristics in the horizontal and vertical axis
Figure 8:
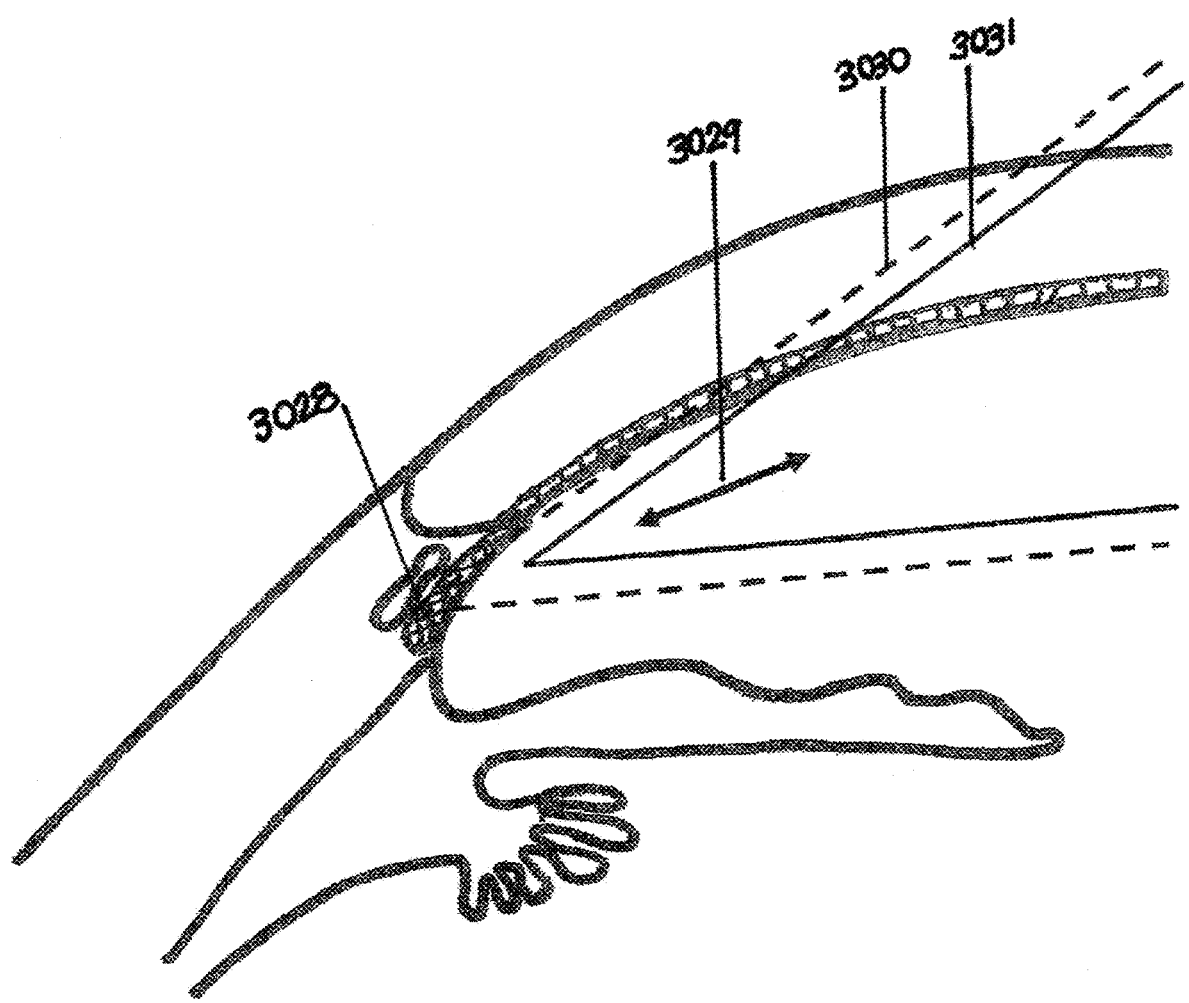
FIG. 8 illustrates a laser focus being scanned back and forward across a tissue interface

Because of significant wave front distortions of the laser beam, as it propagates through various optical and eye anatomical interfaces the coherence quality of the wave front is reduced resulting in a larger spot size. To maintain the same small spot size in the example above the full convergence angle to reach a 3 μm spot size diameter goes up to about 36 degrees (for an $M^2$ of 1.8) as shown in the simulation in FIG. 2.

Furthermore these theoretical values are defined as a $1/e^2$ beam cut off value. If the beam had only exactly that room to propagate and anything outside this envelope would be cut off, then that would result in a larger focus and lost pulse energy due to clipping.

To prevent this additional aberration and energy loss it is important to allow another 5-10 degrees of accessible angle to prevent excessive clipping and to allow for some misalignment margin.

The present invention provides a method for overcoming the limitations described above. In particular the invention provides the following method:

A second method (as named in the parent application) to measure and maximize the vertical angular laser beam access and therefore achieving minimal spot size at the anterior angle tissue layers of an eye. The horizontal convergence angle of the treatment laser beam is fixed to preferably 60 deg (+/−20 deg) to create a small spot size in the horizontal axis in the range of <10 μm diameter depending on the overall aberrations.

Figure 11:
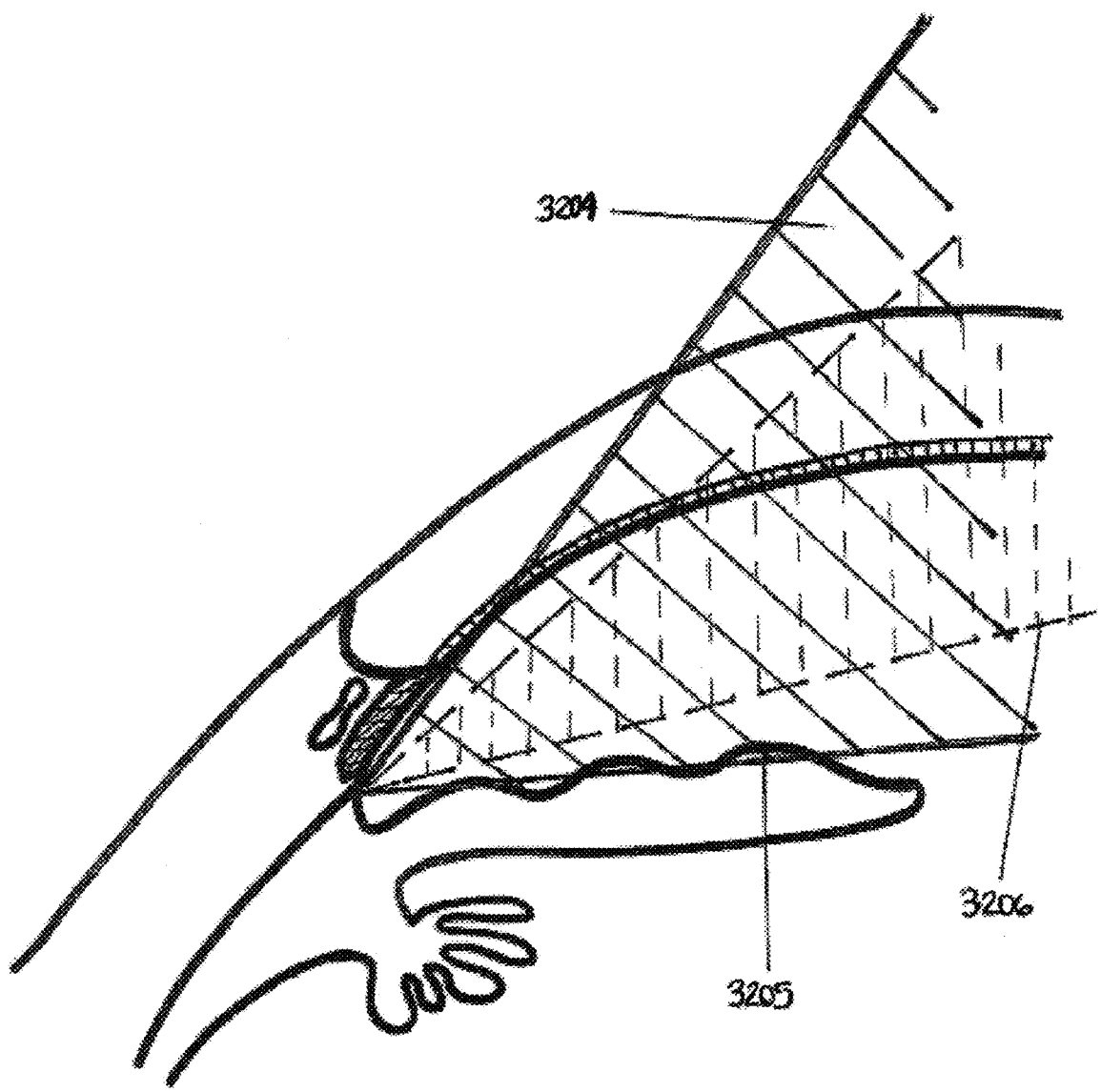
FIG. 11 shows a aiming beam and treatment laser beam focusing into the angle
Figure 12:
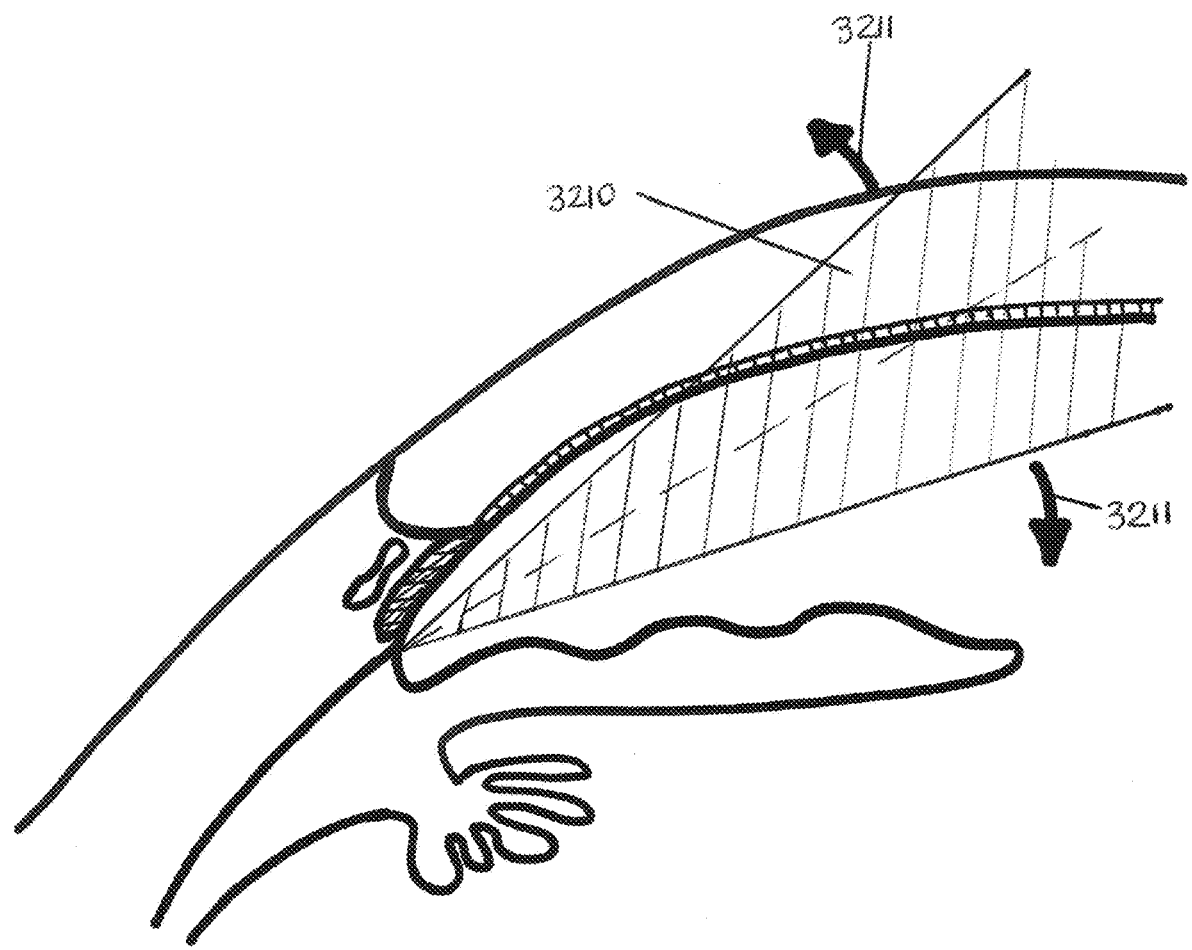
FIG. 12 illustrates an alignment motion for an aiming laser beam
Figure 13:
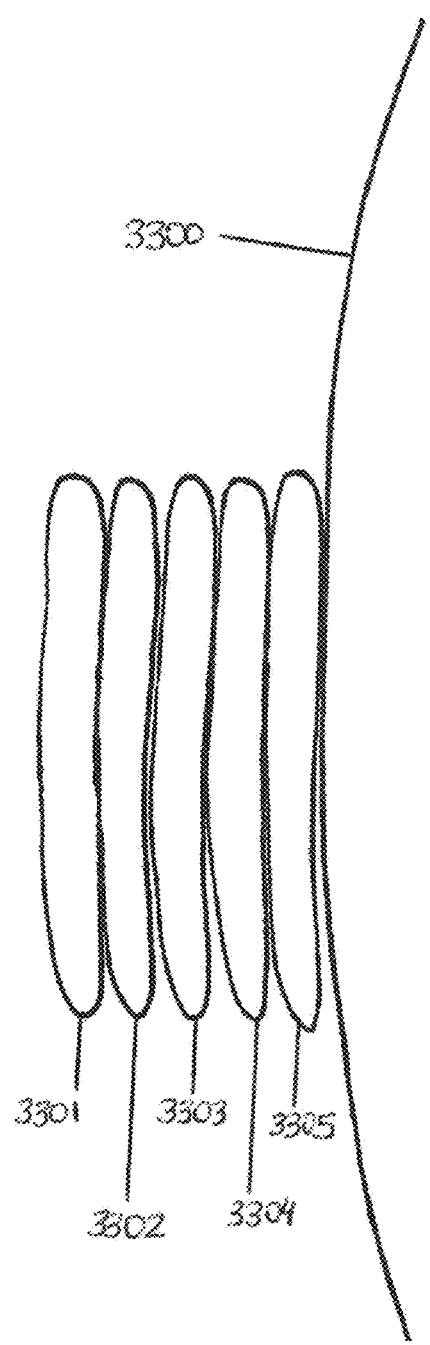
FIG. 13 shows a circular laser firing pattern in the anterior angle tissue layers
Figure 14:
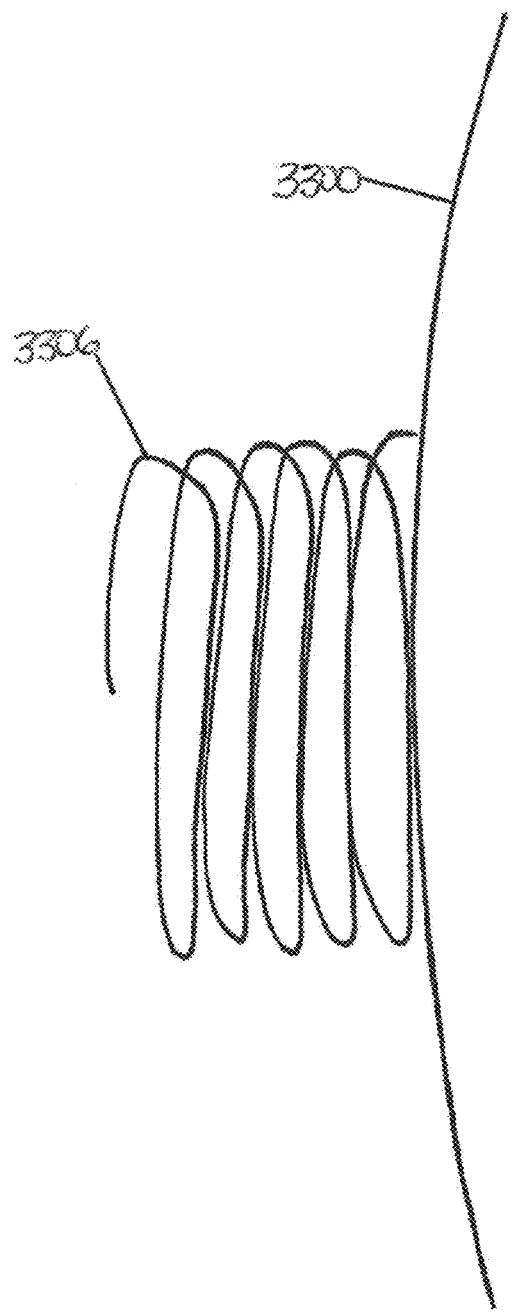
FIG. 14 shows a corkscrew laser firing pattern in the anterior angle tissue layers
Figure 15:
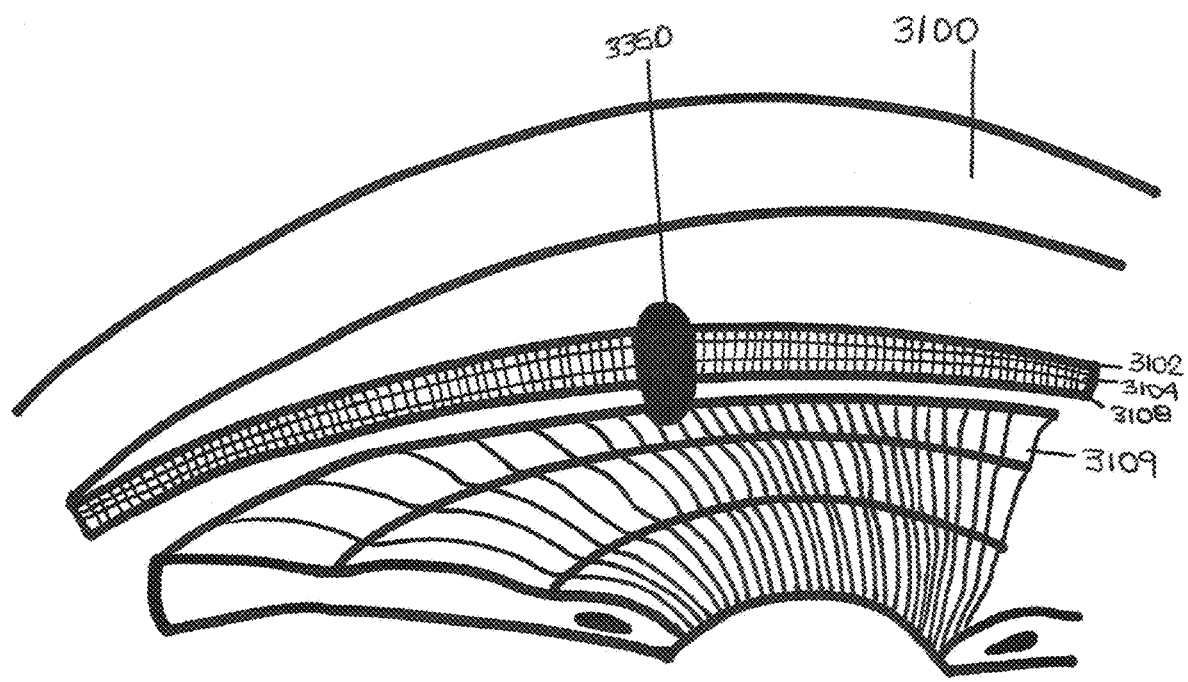
FIG. 15 shows a elliptical photocoagulation zone in the angle of an eye
Figure 16:
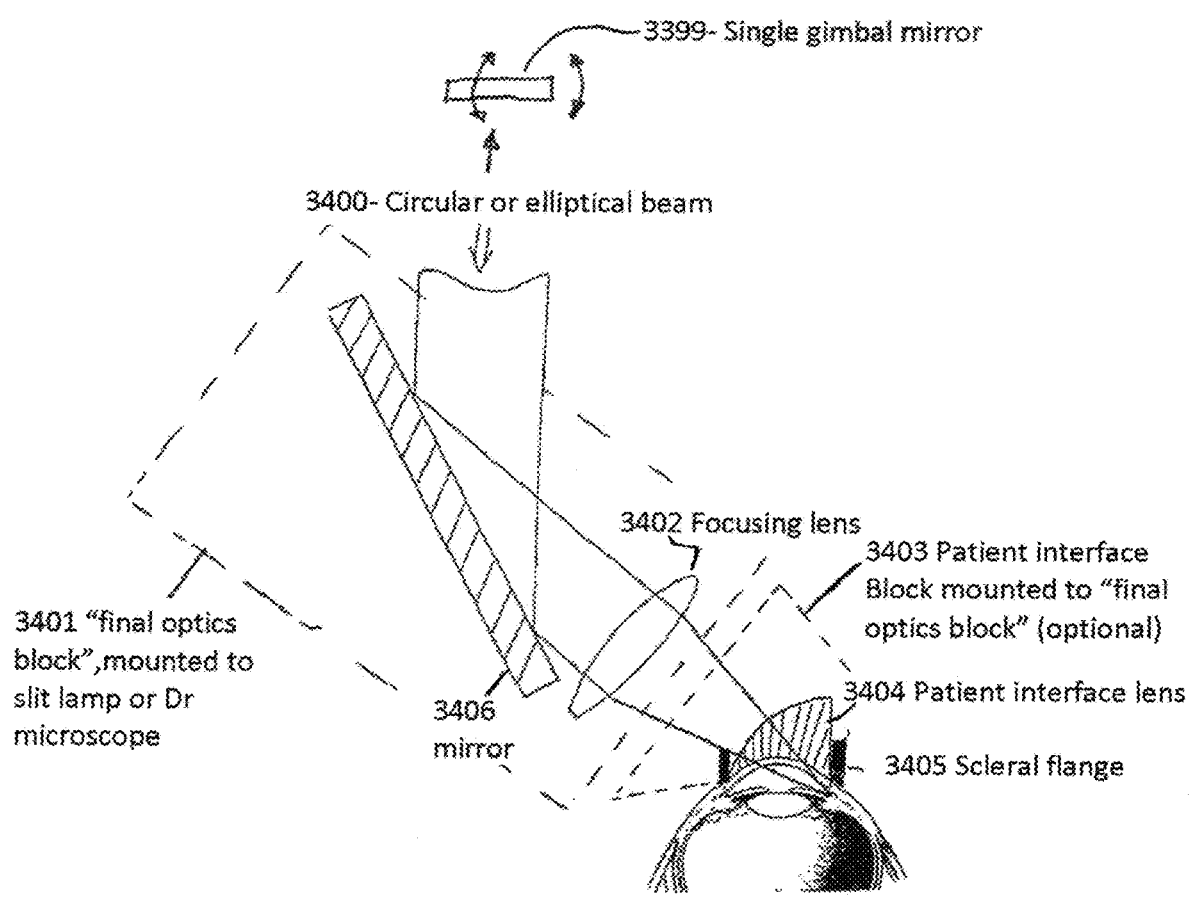
FIG. 16 shows a detailed delivery system design
Figure 17:
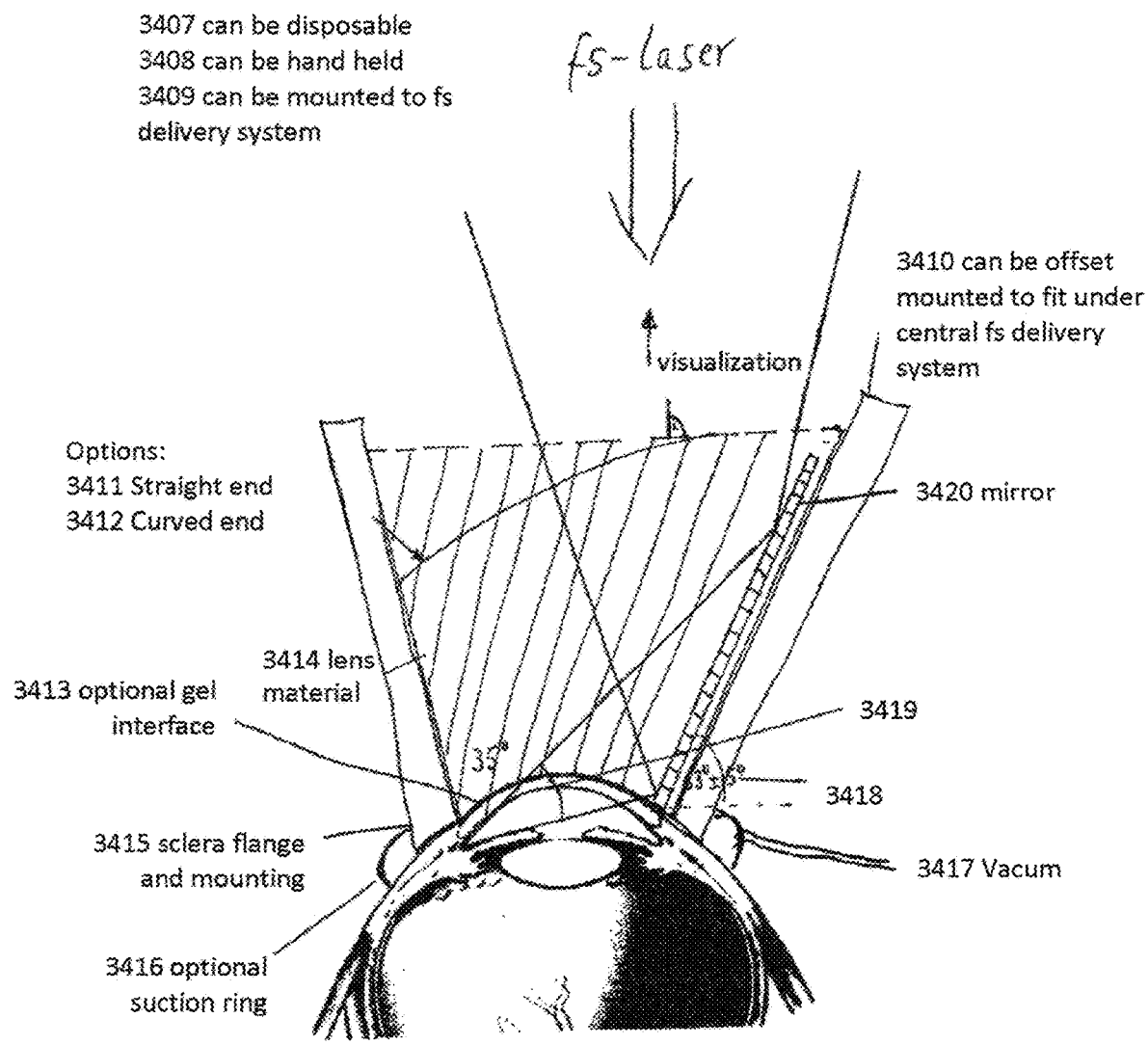
FIG. 17 illustrates a detailed patient interface design
Figure 18:
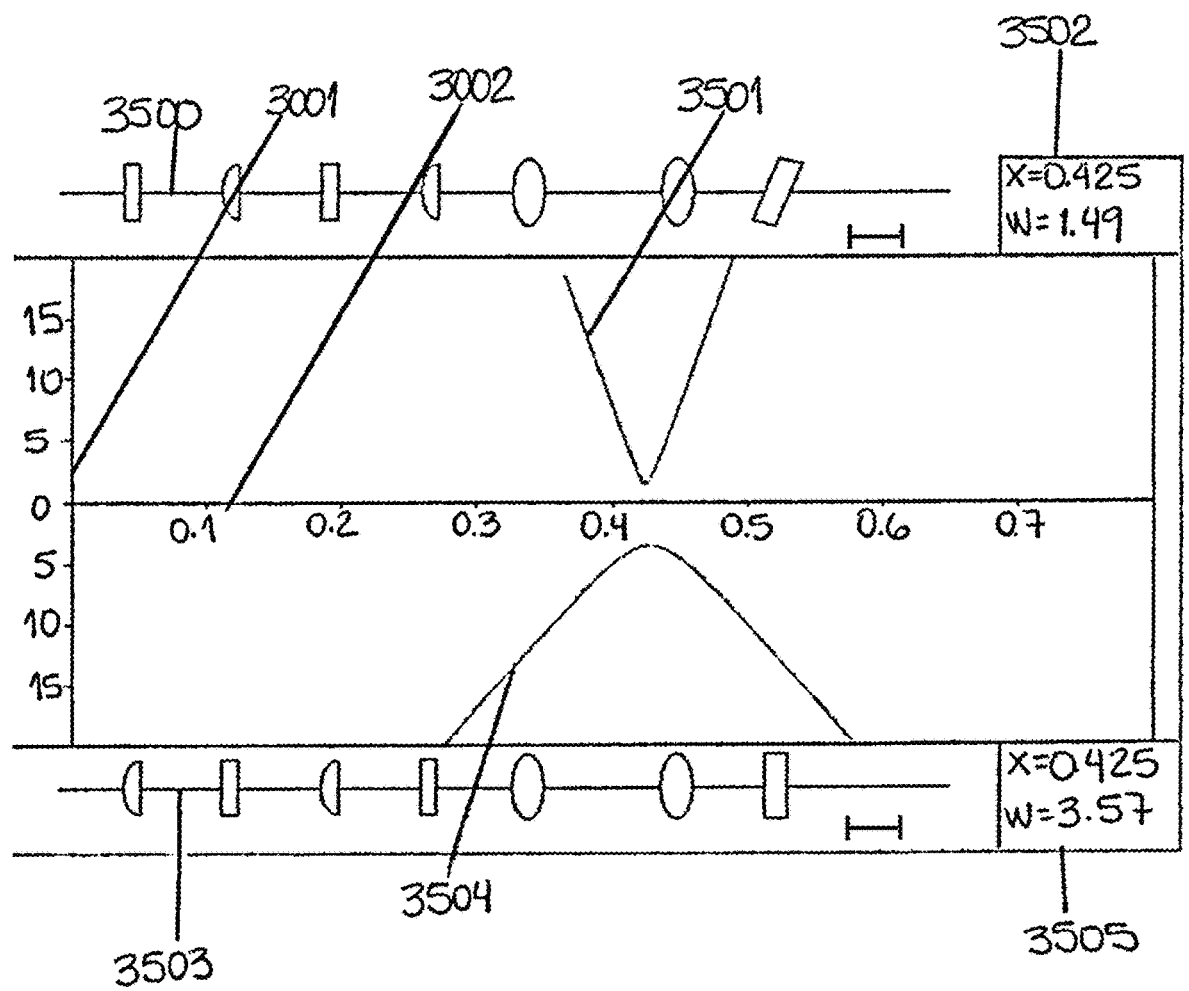
FIG. 18 shows a detailed laser shaping optical delivery system component design
Figure 19:
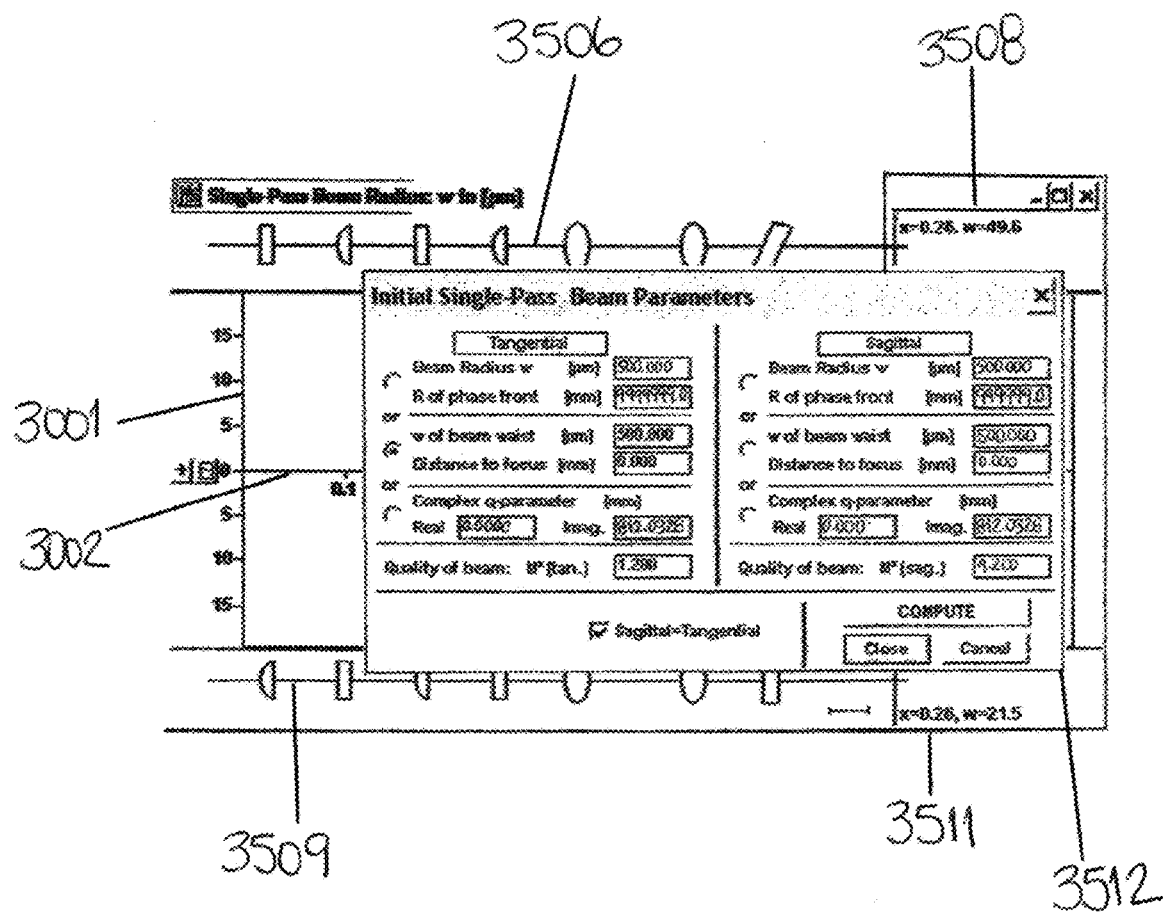
FIG. 19 shows a detailed laser shaping optical delivery system component design
Figure 20:
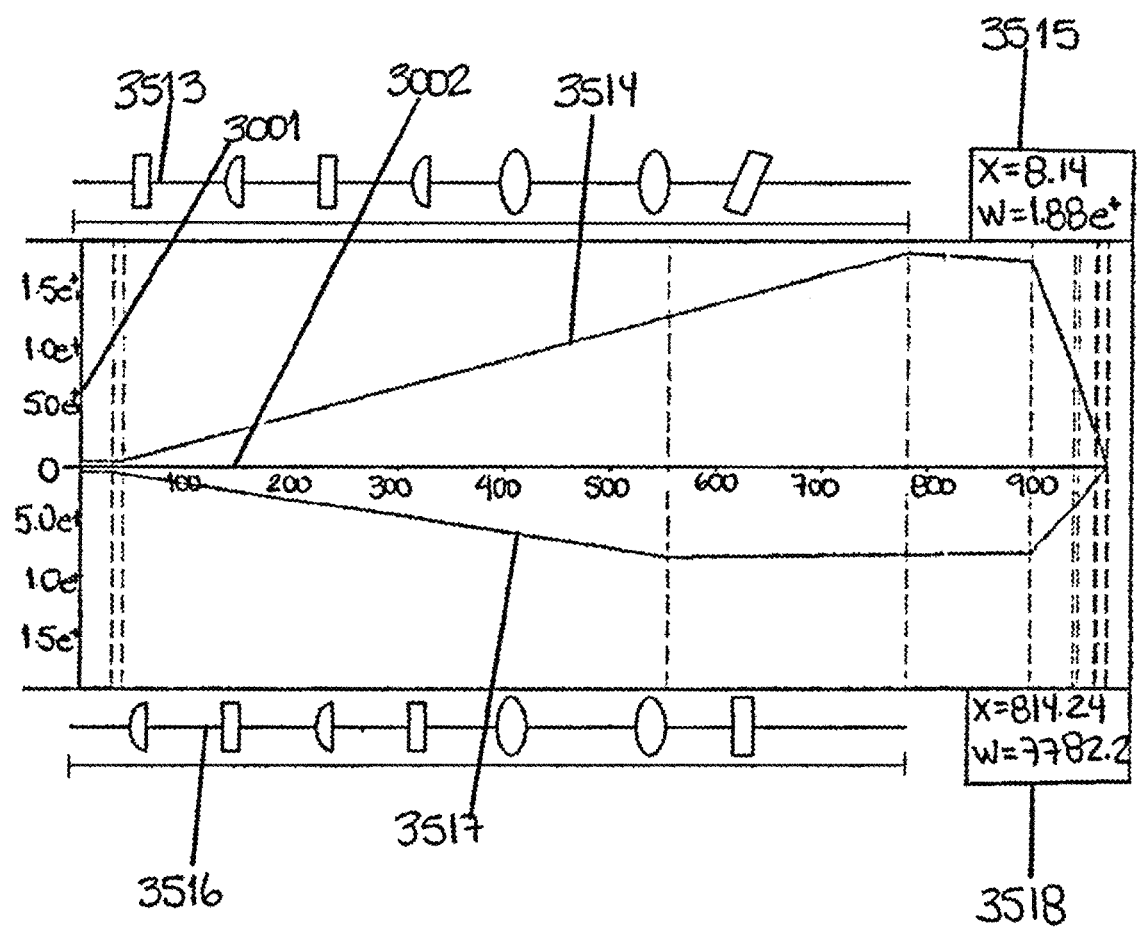
FIG. 20 shows a detailed laser shaping optical delivery system component design
Figure 21:
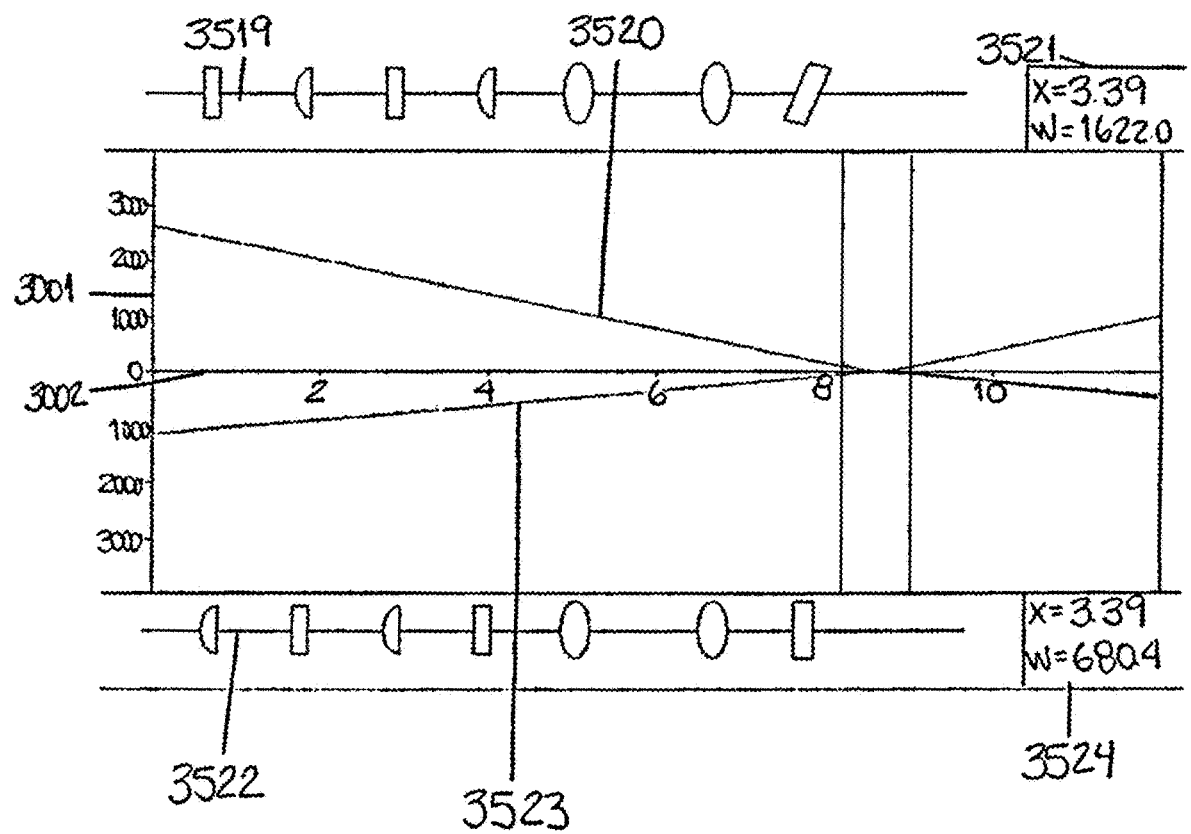
FIG. 21 shows a detailed laser shaping optical delivery system component design
Figure 22:
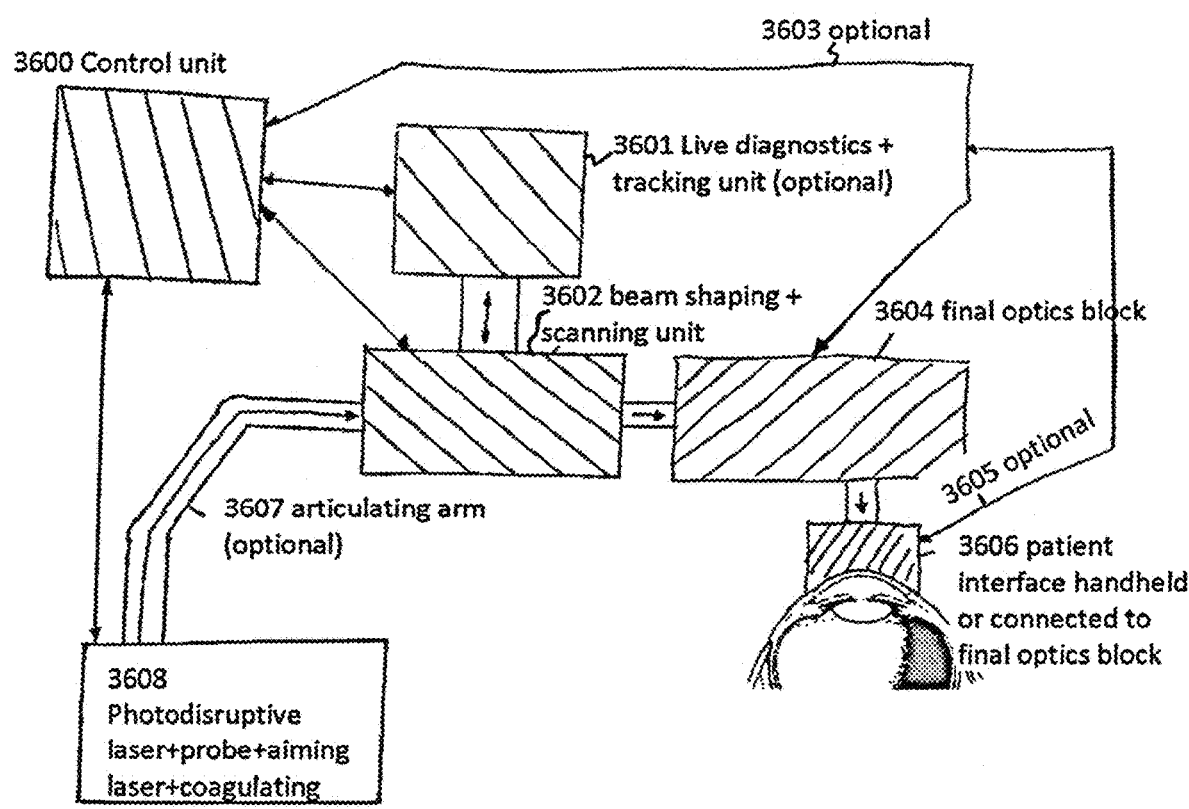
FIG. 22 illustrates a full system block diagram
Figure 23:
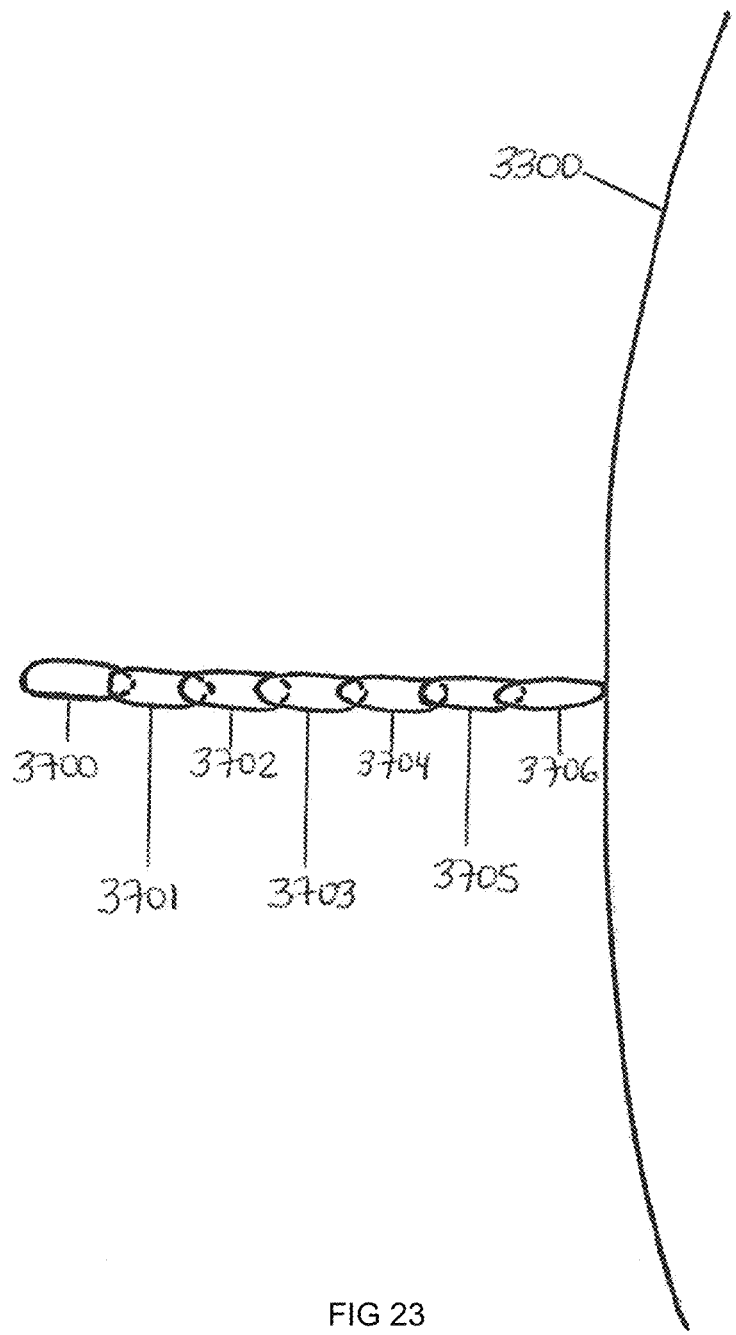
FIG. 23 illustrates a laser firing pattern
Figure 24:
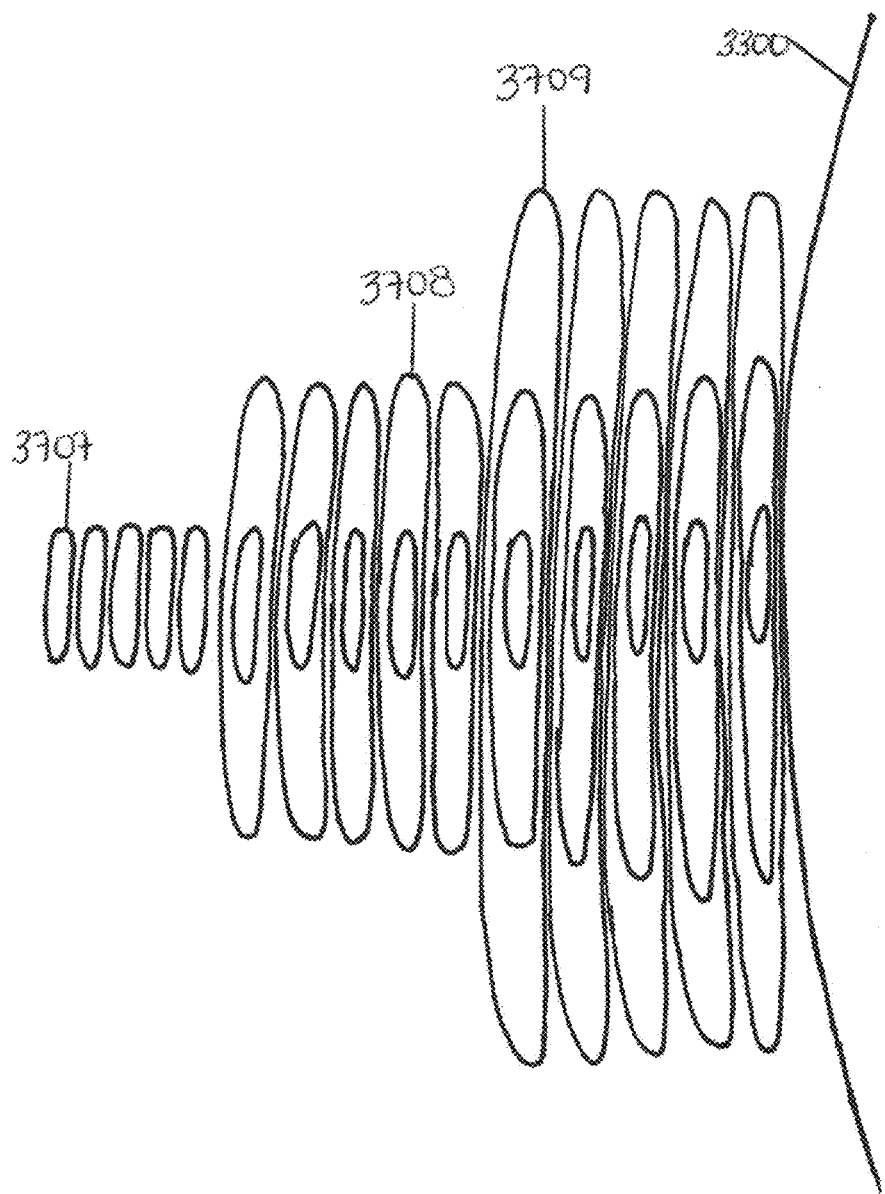
FIG. 24 illustrates a laser firing pattern
Figure 25:
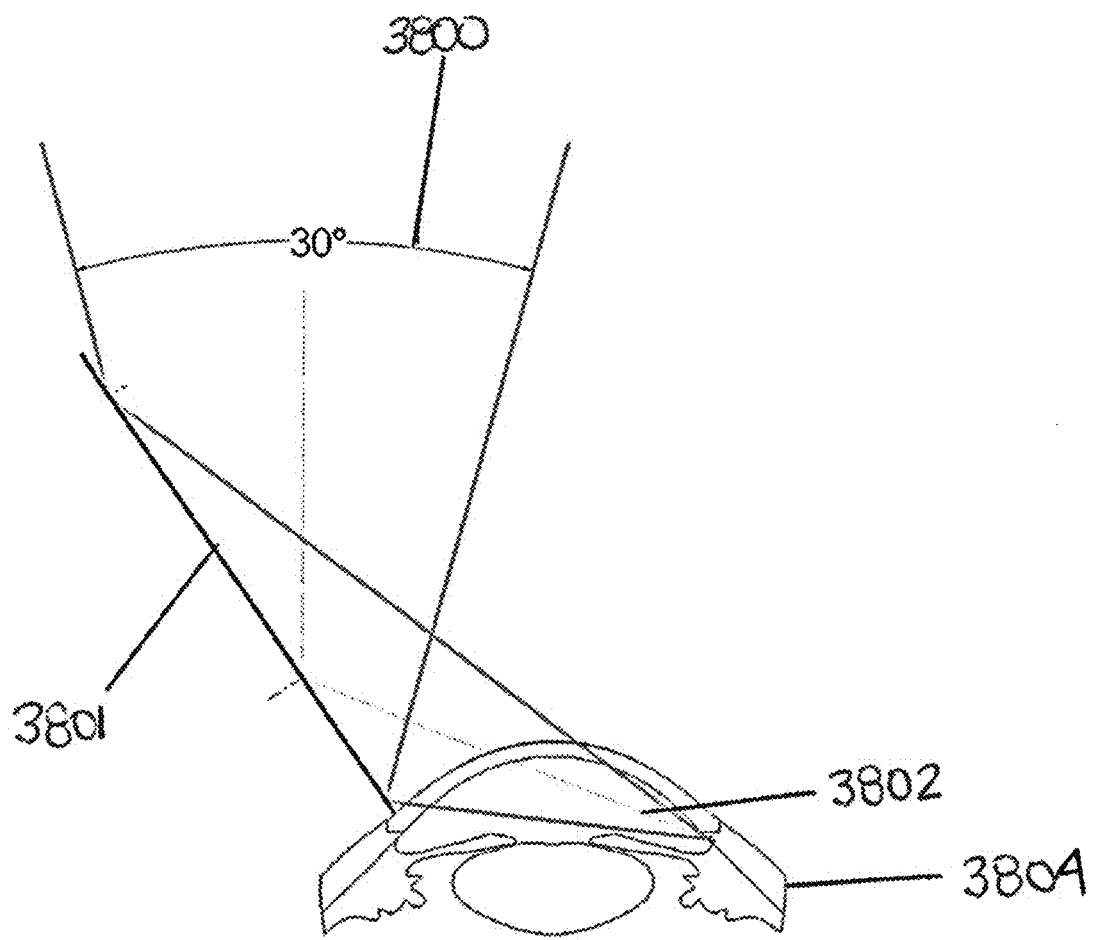
FIG. 25 illustrates the laser beam path of a specific mirror gonio lens

Step a. The angular opening in the vertical axis is determined with the same femtosecond laser delivery system just prior to firing the photodisruptive femtosecond laser pulses by using a shape adjustable visible aiming laser beam under live observation. FIG. 11 shows an aiming laser beam 3204 being focused collinear to the planned photodisruptive treatment beam 3206 into the target tissue layer of the anterior angle of the eye. In one embodiment, this is done by changing the vertical aiming beam divergence from big to small until no light is clipping on the iris and cornea (both sides of the angle) or doing it reverse (small to big) until light starts to scatter on the outside surfaces of the angle. FIG. 11 shows the lower aiming beam envelope clipping on the iris 3205. This scattered light feedback can be observed live by the surgeon/operator or by an automated video/sensor analysis system. While the beam cone is maximized, in the same time the delivery system is preferably constantly adjusted for centration in the angle of the eye to center the focusing beam cone in the angle to achieve the setting of a maximum allowable vertical angle. This adjustment is illustrated in FIG. 12 The beam 3210 is moved in the directions 3211.

Step b. Once the maximum vertical accessibility angle to the target region has been determined the aiming beam is scanned back and forward in the z-axis (above and below the target tissue plane) using a delivery system moving lens (e.g. the main focusing lens) until the visible beam diameter on the target tissue layer is minimized. This minimum spot visualization can be performed live by observation of the surgeon through a microscope or preferably by an automated vision system. The now known z-position of the delivery system optics is now used to calibrate the z-distance of a delivery system reference point to the aiming beam focus position on the surface of the target tissue layer.

Step c. (optional) If the delivery system allows the adjustment of the vertical beam convergence angle for the photodisruptive treatment beam, then the vertical angle is now adjusted to match the maximum determined aiming beam angle from step a. This sets the treatment beam up to achieve a minimum possible vertical spot size on the target tissue layer.

Figure 10:
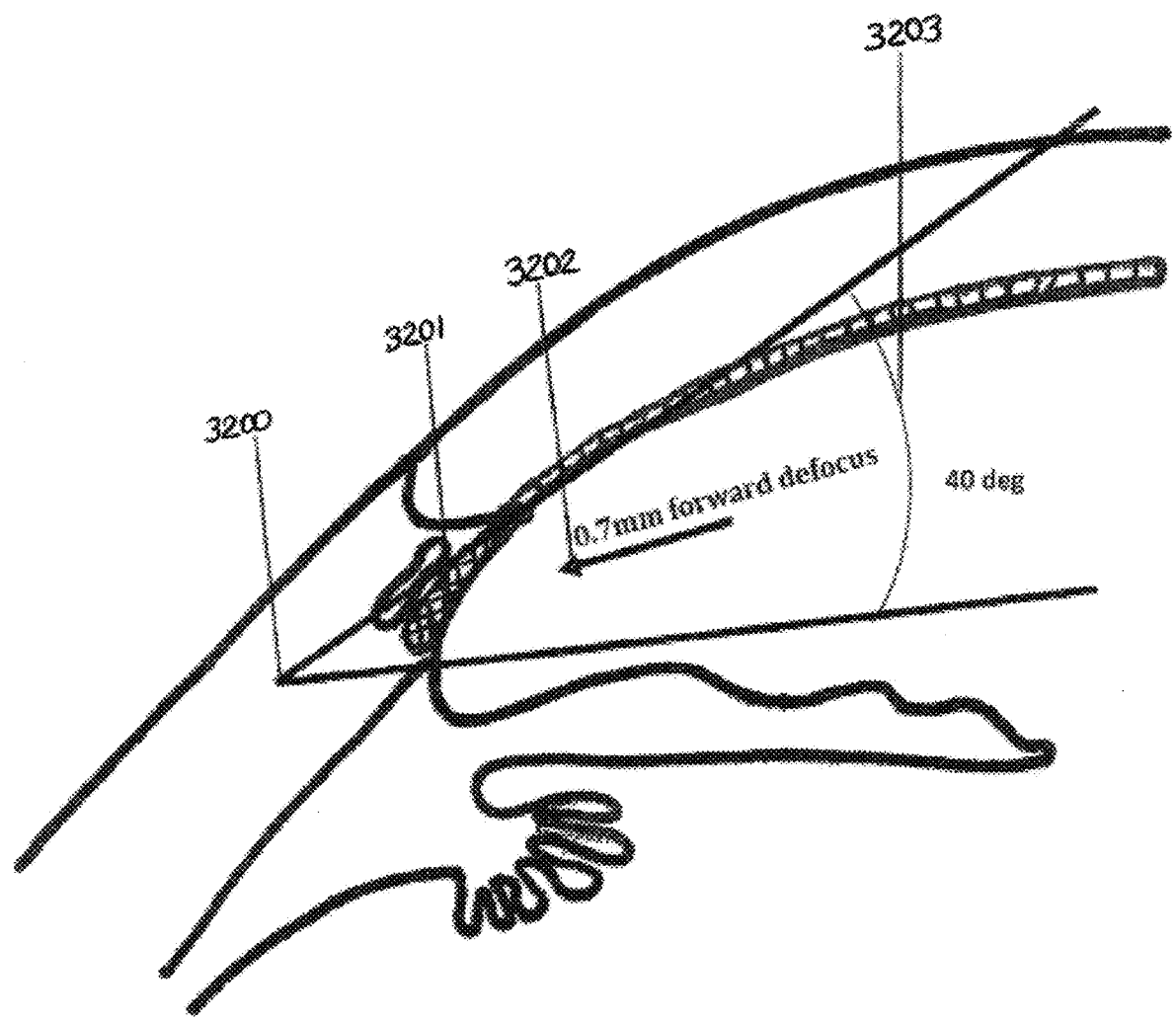
FIG. 10 illustrates a large photocoagulation zone due to a defocused laser beam

Step d. (optional) Photocoagulation of the target tissue area. After the steps a,b and optional c the photodisruptive treatment laser beam is now preferably automatically defocused by a predetermined amount using a z-scan of the focusing lens or other lens in the delivery system. The preferred defocusing adjustment moves the laser focus 0.7 mm (+−0.5 mm) deeper into the target tissue (towards or into the sclera). This results in an enlargement of the laser beam diameter on the target tissue (surface of the anterior angle tissue layer) to about 500 μm FIG. 10, 3201 for a laser beam with a circular convergence angle of 40 deg 3203. After this defocusing adjustment 3202, resulting in a focus position in 3200, the pulse energy is automatically adjusted higher. This pulse energy is adjusted to a level such that the resulting average laser power $P_{average\ power}=E_{laser\ pulse\ energy}R_{laser\ repetition\ rate}$ times the applied laser on duration time during this defocused sequence provides an amount of total energy $E_{total}=P_{average\ power}t_{laser\ on\ duration}$ that photo coagulates the tissue area within the defocused diameter. For a preferred laser repetition rate >100 kHz and a preferred circular area of a 500 μm diameter beam and a preferred laser on duration of <1 s the preferred laser pulse energy is >10 μJ. Lower available pulse energy can be compensated by increasing the laser on duration to achieve the desired amount of photocoagulation. The laser beam area for this defocused large beam (e.g. 500 μm circular diameter) is typically >1000 times larger than typical achieved laser focus on the same surface without defocusing (e.g. 10 μm circular diameter). Therefore any conceivable rise in pulse energy (even to e.g. as high as >500 μJ) would still be far below the plasma threshold energy on this large area. Furthermore the new laser focus 0.7 mm below the anterior angle tissue layer surface is, because of significant photon scattering and absorption of the tissue layers between the surface layer and the 0.7 mm deep layer no longer reaching the fluency level required to exceed the plasma breakdown threshold. All laser power is therefore now absorbed and scattered creating a thermal effect in and around the defocused beam zone leading to photocoagulation versus a photodisruptive cutting effect. The penetration depth of the coagulated tissue volume depends beside the total delivered laser energy also on the laser wavelength. The achieved coagulation zone (volume) reduces or prevents any bleeding from the high fluency (above threshold) laser pulses that follow this step (see step e.) and create a hole or channel into the tissue layers. For a typical photodisruptive (ultra short pulsed) laser wavelength around 1050 nm (+−50 nm) the absorption length is longer than for shorter wavelengths such as used for example in a 532 nm coagulation laser (similar to SLT and ALT). Such a shorter wavelength, quasi cw (continuous wave) laser with a preferred wavelength of 532 nm or 577 nm or 810 nm can be used as a second laser source instead of the defocused photodisruptive main laser. In that configuration the second source shorter wavelength laser does not need to be focused in a highly converging beam since it only needs to reach a preferred spot size diameter of 500 μm (+−300 μm). Furthermore, if another laser is used for the photocoagulation part, than that part of the procedure can be performed before the non-invasive photodisruptive laser procedure. For example the coagulation of one or multiple treatment zones can be performed minutes or days before the channel creating procedure on a laser slit lamp setup. All the above parameter considerations for a preferred circular laser beam are also applicable to a preferred elliptical laser beam.

Step e. The control system of the laser system now calculates and then sets the optimal photodisruptive laser pulse energy based on the input from step a., b. and c. before the treatment laser is fired. The factors for this calculation are as follows: If the vertical treatment beam angle is adjustable then it has been set to the maximum vertical angle in step a. Since the horizontal focusing angle is fixed, the horizontal spot size axis is fixed as well $\omega_0$ horizontal fixed. The vertical spot size $\omega_0$ $_{vertical}$ and therefore the spot size area A is according to formula 1 inverse proportional to the maximum vertical angle $\Theta$.

$$A_{spot\ size\ area} \sim \omega_{0\ horizontal\ fixed} \omega_{0\ vertical} = \omega_{0\ horizontal\ fixed} M_{vertical}^2 \frac{360\ \lambda}{\pi^2 \Theta_{vertical}}$$

with $$\omega_{0\ horizontal\ fixed} = M_{horizontal}^2 \frac{360\ \lambda}{\pi^2 \Theta_{horizontal}}$$

the spot size area A becomes: Formula 2

$$A_{spot\ size\ area} \sim M_{horizontal}^2 \frac{360\ \lambda}{\pi^2 \Theta_{horizontal}} M_{vertical}^2 \frac{360\ \lambda}{\pi^2 \Theta_{vertical}}$$

The required treatment pulse energy is: Formula 3

$$E_{pulse\ energy\ setting} = cE_{threshold\ pulse\ energy}$$

with $E_{threshold\ pulse\ energy}$ being the minimum pulse energy required to achieve a photodisruptive optical breakdown on the desired tissue layer and c being a factor by which the set pulse energy needs to exceed the threshold pulse energy to achieve an efficient photodisruptive tissue effect for cutting and drilling a hole into the tissue layers. The preferred setting for c is 3 to 10. The threshold for the photodisruptive optical 430 breakdown depends on the laser fluency F, being: Formula 4

$$F_{threshold} = \frac{E_{threshold\ pulse\ energy}}{t_{pulse\ duration} A_{spot\ size\ area}}$$

Therefore: $E_{threshold\ pulse\ energy} = F_{threshold} t_{pulse\ duration} A_{spot\ size\ area}$ or: Formula 5

$$E_{threshold\ pulse\ energy} \sim A_{spot\ size\ area}$$

Combining formula 2, 3 and 5 leads to: Formula 6

$$E_{pulse\ energy\ setting} \sim c M_{horizontal}^2 \frac{360\ \lambda}{\pi^2 \Theta_{horizontal}} M_{vertical}^2 \frac{360\ \lambda}{\pi^2 \Theta_{vertical}}$$

If the vertical angle is not adjustable, then it has been set to a fixed preferred angle of $\Theta_{vertical}$=40 deg (+/−15 deg). Depending on the measured maximum vertical accessibility angle in step a. this fixed vertical angle $\Theta_{vertical}$ is either smaller or larger than the maximum accessible angle. If it is larger than the maximum accessible angle then a clipping factor $f_{clip}$ needs to be considered that reduces the laser power on target an enlarges the spot size in the vertical axis. Including this clipping factor the laser control system calculates the required pulse energy setting for the following laser treatment according to Formula 7:

$$E_{pulse\ energy\ setting} \sim f_{clip} c M_{horizontal}^2 \frac{360\ \lambda}{\pi^2 \Theta_{horizontal}} M_{vertical}^2 \frac{360\ \lambda}{\pi^2 \Theta_{vertical}}$$

The beam quality factors $M_{horizontal}^2$ and $M_{vertical}^2$ depend on the sum of all aberrations of the laser system including the delivery system optics, patient interface, patient contact lens (goniolens) the interface to the eye and to some extend the condition of the cornea and anterior chamber of the eye. Most of these beam quality factors are system specific and are preferably calculated and measured. A high level of accuracy in determining those quality factors is achieved by performing photodisruptive laser threshold measurements using model and cadaver eyes on the final laser system setup. The $f_{clip}$ loss factor is also determined by performing photodisruptive laser threshold measurements using model and cadaver eyes on the final laser system setup. They are performed for a range (15 deg to 50 deg) of accessibility angles (step a.) and saved as a table within the laser control system. Once the laser procedure has started and the actual vertical accessibility angle has been determined in step a, the control system looks up the corresponding $f_{clip}$ loss factor and calculates the final laser pulse energy setting $E_{pulse\ energy\ setting}$ according to formula 7.

Step f. After the control system sets the treatment laser pulse energy, the laser will preferably automatically fire a preset scanning pattern with reference to the laser beam alignment in step a. and the z-calibration in step b. to create one or multiple holes into the desired target zone layers (e.g. through the Trabecular Meshwork or into the suprachoroidal space) within the coagulated zone, if created.

Step g. (optional) All steps a. to f. are preferably done in a fully automated sequence immediately following each other and parameters are optimized that the entire laser procedure time is preferably less than 10 s.

Although the present invention has been described in considerable detail with reference to the preferred versions thereof, other versions are possible.

The scope of this patent and the appended claims is limited to the second method as described above. The use of the name "second method" is intended to make it consistent with the parent filing.

The invention claimed is:

1. A method of delivering a laser beam into target tissue layers of an anterior angle of an eye, having a vertical focusing convergence angle that is determined by a measured maximum possible vertical focusing angle for that eye, corresponding to an anterior chamber angle of that eye and having a horizontal focusing convergence angle between 40 and 80 degrees and having a laser treatment energy setting that is optimized for the laser spot size that corresponds to such chosen vertical and horizontal focusing convergence angles and such laser beam creating a channel opening through the target tissue layers.

2. A method of claim 1 where a laser beam additionally is applied to the target tissue layers such that it performs a photocoagulation of the target tissue layers.

3. A method of claim 1 where a z-axis calibration of the target tissue layer relative to a reference point of the delivery system is being created.

4. A method of claim 1 where the channel opening is created through a Trabecular Meshwork, opening a flow channel for an aqueous humor to reach a Schlemm's canal.

5. A method of claim 1 where the channel opening is created through a scleral spur and into a suprachoroidal space to create an outflow channel for an aqueous humor into the suprachoroidal space.

6. A method of claim 1 where all procedure steps are performed fully automated through the use of a control system.

* * * * *